United States Patent
Ingle et al.

(10) Patent No.: US 6,629,535 B2
(45) Date of Patent: *Oct. 7, 2003

(54) NONINVASIVE DEVICES, METHODS, AND SYSTEMS FOR SHRINKING OF TISSUES

(75) Inventors: Frank Ingle, Palo Alto, CA (US); Garry L. Carter, Pleasanton, CA (US); Robert J. Laird, Richmond, CA (US); John P. Claude, San Carlos, CA (US); Paul Do, San Jose, CA (US); Brian J. Mosel, Dublin, CA (US)

(73) Assignee: SURx, Inc., Livermore, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 09/768,985

(22) Filed: Jan. 23, 2001

(65) Prior Publication Data

US 2001/0018606 A1 Aug. 30, 2001

Related U.S. Application Data

(63) Continuation of application No. 09/133,496, filed on Aug. 12, 1998, now Pat. No. 6,216,704, which is a continuation-in-part of application No. 08/910,775, filed on Aug. 13, 1997, which is a continuation-in-part of application No. 08/910,369, filed on Aug. 13, 1997, now Pat. No. 6,035,238, which is a continuation-in-part of application No. 08/910,371, filed on Aug. 13, 1997, now Pat. No. 6,081,749.
(60) Provisional application No. 60/071,418, filed on Jan. 14, 1998, provisional application No. 60/071,419, filed on Jan. 14, 1998, provisional application No. 60/071,422, filed on Jan. 14, 1998, and provisional application No. 60/071,323, filed on Jan. 14, 1998.

(51) Int. Cl.[7] .............................................. A61B 19/00

(52) U.S. Cl. ...................... 128/898; 607/101; 607/105; 606/41

(58) Field of Search ........................... 128/898; 606/41, 606/42, 45, 50; 607/101–105, 138

(56) References Cited

U.S. PATENT DOCUMENTS

| | | |
|---|---|---|
| 373,399 A | 11/1887 | Hamilton |
| 728,883 A | 5/1903 | Downes |
| 3,575,158 A | 4/1971 | Summers |
| 3,749,098 A | 7/1973 | DeBennetot |
| 3,924,631 A | 12/1975 | Mancusi, Jr. |
| 3,926,175 A | 12/1975 | Allen et al. |
| 3,939,821 A | 2/1976 | Roth |
| 4,311,145 A | 1/1982 | Esty et al. |
| 4,381,007 A | 4/1983 | Doss |
| 4,409,453 A | 10/1983 | Smith |
| 4,453,536 A | 6/1984 | Abild |
| 4,679,561 A | 7/1987 | Doss |
| 4,686,962 A | 8/1987 | Haber |
| 4,765,331 A | 8/1988 | Petruzzi et al. |
| 4,773,393 A | 9/1988 | Haber et al. |
| 4,776,344 A | 10/1988 | Shirasaki et al. |
| 4,802,479 A | 2/1989 | Haber et al. |
| 4,807,620 A | 2/1989 | Strul et al. |
| 4,832,680 A | 5/1989 | Haber et al. |
| 4,976,709 A | 12/1990 | Sand |
| 4,994,019 A | 2/1991 | Fernandez et al. |
| 5,003,991 A | 4/1991 | Takayama et al. |
| 5,012,822 A | 5/1991 | Schwarz |
| 5,035,696 A | 7/1991 | Rydell |
| 5,057,106 A | 10/1991 | Kasevich et al. |
| 5,098,429 A | 3/1992 | Sterzer |
| 5,140,999 A | 8/1992 | Ardito |
| 5,190,517 A | 3/1993 | Zieve et al. |
| 5,201,732 A | 4/1993 | Parins et al. |
| 5,234,409 A | 8/1993 | Goldberg et al. |
| 5,256,133 A | 10/1993 | Spitz |
| 5,281,217 A | 1/1994 | Edwards et al. |
| 5,281,218 A | 1/1994 | Imran |
| 5,282,799 A | 2/1994 | Rydell |
| 5,293,869 A | 3/1994 | Edwards et al. |
| 5,304,123 A | 4/1994 | Atala et al. |
| 5,309,910 A | 5/1994 | Edwards et al. |
| 5,314,465 A | 5/1994 | Maurer et al. |
| 5,314,466 A | 5/1994 | Stern et al. |
| 5,330,518 A * | 7/1994 | Neilson et al. ............ 607/101 |
| 5,348,554 A * | 9/1994 | Imran et al. ................. 606/41 |
| 5,366,490 A | 11/1994 | Edwards et al. |
| 5,370,675 A | 12/1994 | Edwards et al. |
| 5,370,677 A | 12/1994 | Rudie et al. |
| 5,370,678 A | 12/1994 | Edwards et al. |
| 5,376,064 A | 12/1994 | Cerny |

| | | |
|---|---|---|
| 5,385,544 A | 1/1995 | Edwards et al. |
| 5,403,312 A | 4/1995 | Yates et al. |
| 5,405,346 A | 4/1995 | Grundy et al. |
| 5,411,475 A | 5/1995 | Atala et al. |
| 5,417,208 A | 5/1995 | Winkler |
| 5,423,811 A | 6/1995 | Imran et al. |
| 5,431,649 A | 7/1995 | Mulier et al. |
| 5,437,603 A | 8/1995 | Cerny et al. |
| 5,437,664 A | 8/1995 | Cohen et al. |
| 5,447,529 A | 9/1995 | Marchlinski et al. |
| 5,454,809 A | 10/1995 | Janssen |
| 5,458,596 A * | 10/1995 | Lax et al. ............... 606/31 |
| 5,462,545 A | 10/1995 | Wang et al. |
| 5,480,417 A | 1/1996 | Hascoet et al. |
| 5,496,312 A | 3/1996 | Klicek |
| 5,514,130 A | 5/1996 | Baker |
| 5,533,999 A | 7/1996 | Hood et al. |
| 5,536,267 A | 7/1996 | Edwards et al. |
| 5,540,655 A | 7/1996 | Edwards et al. |
| 5,540,679 A | 7/1996 | Fram et al. |
| 5,542,916 A | 8/1996 | Hirsch et al. |
| 5,545,137 A * | 8/1996 | Rudie et al. ........... 604/102.01 |
| 5,549,644 A | 8/1996 | Lundquist et al. |
| 5,554,110 A | 9/1996 | Edwards et al. |
| 5,569,242 A | 10/1996 | Lax et al. |
| 5,588,960 A | 12/1996 | Edwards et al. |
| 5,591,125 A | 1/1997 | Edwards et al. |
| 5,609,598 A | 3/1997 | Laufer et al. |
| 5,611,515 A | 3/1997 | Benderev et al. |
| 5,628,770 A | 5/1997 | Thome et al. |
| 5,649,973 A | 7/1997 | Tierney et al. |
| 5,667,488 A | 9/1997 | Lundquist et al. |
| 5,673,695 A | 10/1997 | McGee et al. |
| 5,687,723 A | 11/1997 | Avitall |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,746,224 A * | 5/1998 | Edwards ............... 128/898 |
| 5,755,753 A | 5/1998 | Knowlton |
| 5,769,879 A | 6/1998 | Richards et al. |
| 5,769,880 A | 6/1998 | Truckai et al. |
| 5,792,140 A | 8/1998 | Tu et al. |
| 5,807,395 A | 9/1998 | Mulier et al. |
| 5,810,847 A | 9/1998 | Laufer et al. |
| 5,843,077 A | 12/1998 | Edwards |
| 5,871,524 A * | 2/1999 | Knowlton ............... 606/27 |
| 5,879,348 A | 3/1999 | Owens et al. |
| 5,895,417 A | 4/1999 | Pomeranz et al. |
| 5,919,219 A | 7/1999 | Knowlton |
| 5,948,011 A | 9/1999 | Knowlton |
| 5,957,920 A | 9/1999 | Baker |
| 6,015,406 A | 1/2000 | Goble et al. |
| 6,015,407 A | 1/2000 | Rieb et al. |
| 6,035,238 A | 3/2000 | Ingle et al. |
| 6,044,846 A | 4/2000 | Edwards |
| 6,044,847 A | 4/2000 | Carter et al. |
| 6,081,749 A | 6/2000 | Ingle et al. |
| 6,091,995 A | 7/2000 | Ingle et al. |
| 6,104,959 A * | 8/2000 | Spertell ............... 606/31 |
| 6,139,569 A | 10/2000 | Ingle et al. |
| 6,156,060 A | 12/2000 | Roy et al. |
| 6,216,704 B1 | 4/2001 | Ingle et al. |
| 6,236,891 B1 | 5/2001 | Ingle et al. |
| 6,241,753 B1 | 6/2001 | Knowlton |
| 6,273,886 B1 | 8/2001 | Edwards et al. |
| 6,283,987 B1 | 9/2001 | Laird et al. |
| 6,292,700 B1 | 9/2001 | Morrison et al. |
| 6,322,584 B2 | 11/2001 | Ingle et al. |
| 6,334,074 B1 * | 12/2001 | Spertell ............... 606/31 |
| 6,413,253 B1 * | 7/2002 | Koop et al. ............... 606/10 |
| 6,416,504 B2 | 7/2002 | Mosel et al. |

FOREIGN PATENT DOCUMENTS

| | | |
|---|---|---|
| WO | WO 93/07815 | 4/1993 |
| WO | WO 93/15664 A1 | 8/1993 |
| WO | WO 96/00041 | 1/1996 |
| WO | WO 96/00042 | 1/1996 |
| WO | WO 96/34568 | 11/1996 |
| WO | WO 97/15238 | 5/1997 |
| WO | WO 97/20510 | 6/1997 |
| WO | WO 97/24992 | 7/1997 |
| WO | WO 97/32532 | 9/1997 |
| WO | WO 97/39688 | 10/1997 |
| WO | WO 97/43970 | 11/1997 |
| WO | WO 97/43971 | 11/1997 |
| WO | Wo 98/05286 | 2/1998 |
| WO | WO 98/05380 | 2/1998 |
| WO | WO 98/07468 | 2/1998 |
| WO | WO 98/38936 | 9/1998 |
| WO | WO 99/16502 | 5/1999 |
| WO | WO 01/22897 | 4/2001 |

OTHER PUBLICATIONS

Hayes et al., "Prediction of Transient Temperature Fields and Cumulative Tissue Destruction for Radio Frequency Heating of a Tumor" *Med. Phys.* 12:6 (Nov./Dec. 1995) pp. 684–692.

* cited by examiner

*Primary Examiner*—Michael Peffley
(74) *Attorney, Agent, or Firm*—Townsend and Townsend and Crew, LLP

(57) ABSTRACT

The invention provides improved devices, methods, and systems for shrinking of collagenated tissues, particularly for treating urinary incontinence in a noninvasive manner by directing energy to a patient's own support tissues. This energy heats fascia and other collagenated support tissues, causing them to contract. The energy can be applied intermittently, often between a pair of large plate electrodes having cooled flat electrode surfaces, the electrodes optionally being supported by a clamp structure. Such cooled plate electrodes are capable of directing electrical energy through an intermediate tissue and into fascia while the cooled electrode surface prevents injury to the intermediate tissue, particularly where the electrode surfaces are cooled before, during, and after an intermittent heating cycle. Ideally, the plate electrode comprises an electrode array including discrete electrode surface segments so that the current flux can be varied to selectively target the fascia. Alternatively, chilled "liquid electrodes" may direct current through a selected portion of the bladder (or other body cavity) while also cooling the bladder wall, an insulating gas can prevent heating of an alternative bladder portion and the adjacent tissues, and/or ultrasound transducers direct energy through an intermediate tissue and into fascia with little or no injury to the intermediate tissue. Cooled electrodes may be used to chill an intermediate engaged tissue so as to cause the maximum temperature difference between the target tissue and the intermediate tissue prior to initiating RF heating. This allows the dimensions of tissue reaching the treatment temperature to be controlled and/or minimized, the dimensions of protected intermediate tissue to be maximized, and the like.

19 Claims, 24 Drawing Sheets

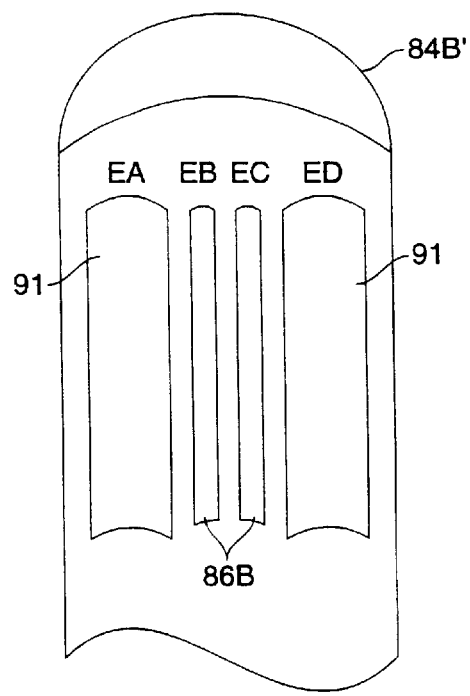
FIG. 12Di
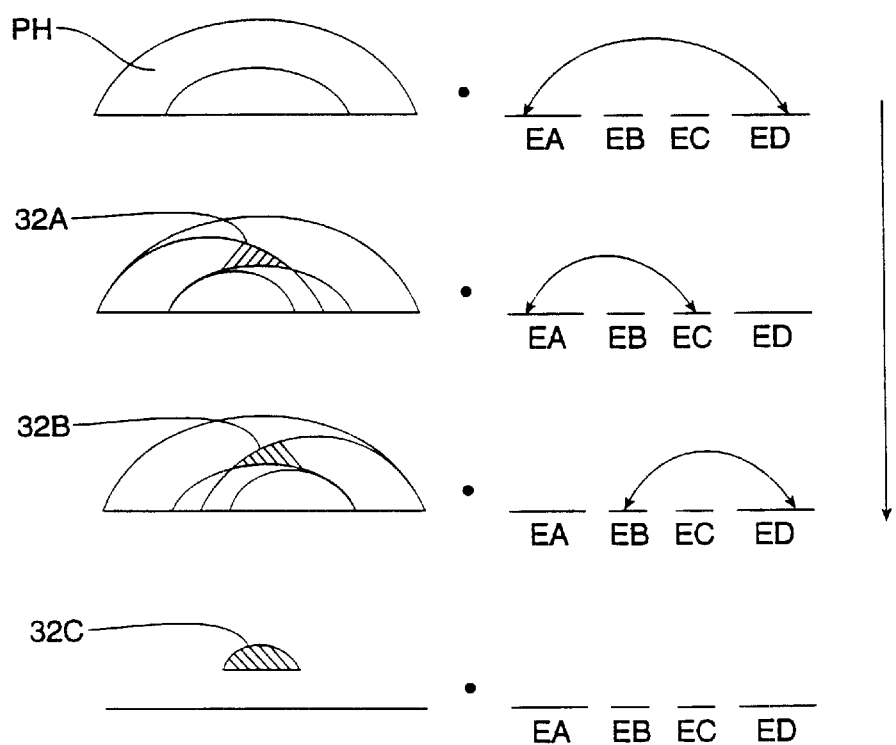
FIG. 12Dii

NONINVASIVE DEVICES, METHODS, AND SYSTEMS FOR SHRINKING OF TISSUES

CROSS-REFERENCES TO RELATED APPLICATIONS

This application is a continuation of and claims the benefit of priority from U.S. patent application Ser. No. 09/133,496 filed Aug. 12, 1998 now U.S. Pat. No. 6,216,704, which is a continuation-in-part of U.S. patent application Ser. Nos. 08/910,775; 08/910,369 now U.S. Pat. No. 6,035,238, and 08/910,371 now U.S. Pat. No. 6,081749, all filed Aug. 13, 1997, and U.S. Provisional Patent Application Nos. 60/071,418; 60/071,419; 60/071,422; and 60/071,323, all filed Jan. 14, 1998, the full disclosures of which are incorporated herein by reference.

This application is also related to co-pending U.S. patent application Ser. No. 09/765,923 filed Jan. 19, 2001 (Attorney Docket No. 17761-000371US), the full disclosure of which is incorporated herein by reference.

BACKGROUND OF THE INVENTION

1. Field of the Invention

The present invention generally relates to medical devices, methods, and systems. More specifically, the present invention provides techniques for selectively heating and shrinking tissues, particularly for the noninvasive treatment of urinary incontinence and hernias, for cosmetic surgery, and the like.

Urinary incontinence arises in both women and men with varying degrees of severity, and from different causes. In men, the condition occurs most often as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such non-interventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

A variety of other problems can arise when the support tissues of the body have excessive length. Excessive length of the pelvic support tissues (particularly the ligaments and fascia of the pelvic area) can lead to a variety of ailments including, for example, cystocele, in which a portion of the bladder protrudes into the vagina. Excessive length of the tissues supporting the breast may cause the breasts to sag. Many hernias are the result of a strained, torn, and/or distended containing tissue, which allows some other tissue or organ to protrude beyond its contained position. Cosmetic surgeries are also often performed to decrease the length of support tissues. For example, abdominoplasty (often called a "tummy tuck") is often performed to decrease the circumference of the abdominal wall. The distortion of these support tissues may be due to strain, advanced age, congenital predisposition, or the like.

Unfortunately, many support tissues are difficult to access, and their tough, fibrous nature can complicate their repair. As a result, the therapies now used to improve or enhance the support provided by the ligaments and fascia of the body often involve quite invasive surgical procedures.

For these reasons, it would be desirable to provide improved devices, methods, and systems for treating fascia, tendons, and the other support tissues of the body. It would be particularly desirable to provide improved noninvasive or minimally invasive therapies for these support tissues, especially for the treatment of urinary incontinence in men and women. It would further be desirable to provide treatment methods which made use of the existing support structures of the body, rather than depending on the specific length of an artificial support structure.

2. Description of the Background Art

U.S. Pat. No. 5,423,811 describes a method for RF ablation using a cooled electrode. U.S. Pat. Nos. 5,458,596 and 5,569,242 describe methods and an apparatus for controlled contraction of soft tissue. An RF apparatus for controlled depth ablation of soft tissue is described in U.S. Pat. No. 5,514,130.

U.S. Pat. No. 4,679,561 describes an implantable apparatus for localized heating of tissue, while U.S. Pat. No. 4,765,331 describes an electrosurgical device with a treatment arc of less than 360 degrees. An impedance and temperature generator control is described in U.S. Pat. No. 5,496,312. Bipolar surgical devices are described in U.S. Pat. Nos. 5,282,799, 5,201,732, and 728,883.

SUMMARY OF THE INVENTION

The present invention provides devices, methods, and systems for shrinking of collagenated tissues, particularly for treating urinary incontinence in a noninvasive manner. In contrast to prior art techniques, the present invention does not rely on implantation of balloons or other materials, nor does it rely on suturing, cutting, or other direct surgical modifications to the natural support tissues of the body. Instead, the present invention directs energy to a patient's own support tissues. This energy heats fascia and other collagenated support tissues, causing them to contract without substantial necrosis of adjacent tissues. The energy will preferably be applied through a large, cooled electrode having a substantially flat electrode surface. Such a cooled plate electrode is capable of directing electrical energy through an intermediate tissue and into fascia, while the cooled electrode surface prevents injury to the intermediate tissue. Ideally, the plate electrode comprises an electrode array which includes several discrete electrode surface segments so that the current flux can be varied to selectively target and evenly heat the fascia. In some embodiments, the tissue is heated between a pair of parallel cooled electrode surfaces, the parallel surfaces optionally being planar, cylindrical, spherical, or the like. Alternatively, the tissue may be treated with a bipolar probe, particularly after pre-cooling the intermediate tissue to selectively vary tissue impedance and thereby direct the heating current through the target tissue.

In a first aspect, the present invention provides a probe for therapeutically heating a target tissue of a patient body through an intermediate tissue. The probe comprises an electrode with an electrode surface which is engageable against the intermediate tissue. The electrode surface is substantially flat, and a cooling system is coupled to the electrode. The cooling system allows the electrode surface to cool the engaged intermediate tissue while an electrical current flux from the electrode surface therapeutically heats the target tissue.

The electrode surface will generally be sufficiently flat to direct the current flux through the cooled intermediate tissue and into the target tissue while the cooling system maintains the intermediate tissue at or below a maximum safe tissue temperature. To direct the current flux, heating may be provided between a pair of electrode surfaces, the electrode surfaces typically being separated by a distance from about ⅓ to about 5.0 times the least width of the electrodes, preferably being separated by a distance from about ½ to about 2.0 times the least electrode width. In many embodiments, a temperature sensor will monitor the temperature of the target tissue or the intermediate tissue. A control system will often selectively energize the electrode and/or cooling system in response to the monitored temperature.

In another aspect, the present invention provides a probe for applying energy to fascia from within the vagina of a patient body. The fascia is separated from the vagina by a vaginal wall. The probe comprises a probe body having a proximal end and a distal end, the probe having a length and a cross-section selected to permit introduction into the vagina. An energy transmitting element is mounted to the probe body. The transmitting element is capable of transmitting sufficient heating energy through the vaginal wall to heat and contract the fascia. A cooling system is disposed adjacent to the transmitting element. The cooling system is capable of maintaining the vaginal wall adjacent the probe below a maximum safe temperature when the fascia is heated by the transmitting element.

The present invention also provides a method for shrinking a target collagenated tissue within a patient body through an intermediate tissue. The method comprises directing energy from a probe, through the intermediate tissue, and into the target tissue. The energy heats the target tissue so that the target tissue contracts. The intermediate tissue is cooled with the probe to avoid injuring the intermediate tissue when the target tissue is heated by the probe.

In yet another aspect, the present invention provides a method for directing energy into a target tissue of a patient body through an intermediate tissue. The method comprises electrically coupling a first electrode to the patient body. A second electrode is electrically coupled to the intermediate tissue, the second electrode being mounted on a probe. The intermediate tissue is cooled by the probe, and an electrical potential is applied between the first and second electrodes. An electrode surface of the second electrode is sufficiently large and flat to provide a current flux that extends through the cooled intermediate tissue so that the current flux heats the target tissue.

In yet another aspect, the present invention provides a method for therapeutically heating a target zone of a tissue within a patient body. The method comprises engaging a tissue adjacent to the target zone with a probe. The adjacent tissue is pre-cooled with the probe, and the target zone is heated by directing energy from the probe, through the pre-cooled adjacent tissue, and into the target zone.

In another aspect, the present invention provides a kit for shrinking a target collagenated tissue within a patient body through an intermediate tissue. The kit comprises a probe having an energy transmitting element adapted to direct an energy flux through the intermediate tissue and into the target tissue. A cooling system is adjacent to the transmitting element to cool the intermediate tissue. The kit also includes instructions for operating the probe. The instructions comprise the steps of directing energy from the energy transmitting element of the probe, through the intermediate tissue, and into the target tissue so as to heat and shrink the target tissue. The intermediate tissue is cooled with the cooling system of the probe to avoid injuring the intermediate tissue.

In a further aspect, the present invention further provides a method for teaching. The method comprises demonstrating cooling of a surface with a probe. Directing of energy from the probe is also demonstrated, the energy being directed through the surface and into the underlying structure to effect shrinkage of the structure.

In yet another aspect, the present invention provides a system for therapeutically heating a target zone within a tissue. The system comprises a first electrode having a first electrode surface which is engageable against the tissue. A second electrode has a second electrode surface which can be aligned substantially parallel to the first electrode surface, with the tissue positioned therebetween. An electrical current flux between these parallel electrodes can substantially evenly heat the target zone. A cooling system is coupled to at least one of the electrodes for cooling the electrode surface. Generally, radiofrequency current is used to avoid tissue stimulation.

In another aspect, the present invention provides a method for therapeutically heating a target zone of a patient body. The target zone is disposed within a tissue between first and second tissue surfaces. The method comprises engaging a first electrode surface against the first tissue surface. A second electrode surface is aligned substantially parallel with the first electrode surface and against the second tissue surface. An electrical potential is applied between the first and second electrodes so as to produce an electrical current flux which heats the target zone. At least one of the first and second tissue surfaces is cooled by the engaged electrode.

The present invention also provides a probe for heating a target tissue of a patient body through an intermediate tissue. The probe comprises a probe body supporting an electrode array. The electrode array includes a plurality of electrode surface segments. The electrode surface segments are simultaneously engageable against the intermediate tissue, and a cooling system is coupled to the probe for cooling the electrode surface segments. A control system is also coupled to the electrode surface segments. The control system is adapted to selectively energize the electrode surface segments so as to heat the target tissue to a treatment temperature while the cooling system maintains the intermediate tissue (which is disposed between the electrode array and the target zone) at or below a maximum safe tissue temperature.

In another aspect, the present invention provides a method for therapeutically heating a target zone of a tissue within a patient body. The method comprises engaging a probe against the tissue. The probe has a plurality of electrode surface segments, and the tissue is cooled adjacent the probe by the electrode surface segments. An electrical current flux is directed from the electrode surface segments, through the cooled tissue, and into the target zone by selectively energizing the electrode surface segments so that the current flux substantially evenly heats the target zone.

In some embodiments of the present invention, tissue contraction energy will preferably be in the form of a radio frequency (RF) electrical current applied through an electrolytic solution. Often times, the electrolytic solution will be introduced into the patient's bladder through a transurethral probe, and will provide electrical coupling between an electrode of the probe and the bladder wall. To enhance control over the therapeutic heating and shrinking of tissues applied internally through an electrolytic solution, a controlled volume of both the electrolytic solution and an electrically and thermally insulating gas can be introduced into the patient's bladder (or some other hollow body organ). By orienting the patient so that the electrically conductive solution is positioned within the bladder adjacent the pelvic support tissues, the conductive solution can transmit electrical current over a relatively large and fairly well controlled interface between the conductive solution and the bladder wall, while the gas prevents transmission of the RF energy to the delicate abdominal tissues above the bladder. The electrically conductive solution may also provide direct cooling of the bladder wall before, during, and/or after the therapeutically heating RF energy is transmitted. Such cooling may be enhanced by circulating chilled conductive solution through the bladder, optimizing the electrical properties of the solution to minimize heat generated within the solution, and the like. In the exemplary embodiment, the RF energy is transmitted between the electrolyte/bladder wall interface and a cooled, substantially flat electrode of a vaginal probe so as to shrink the endopelvic fascia therebetween and thereby inhibit incontinence.

In this aspect of the present invention, a method for heating a target tissue within a patient body heats tissue separated from a body cavity by an intermediate tissue. The method comprises introducing a conductive fluid into the cavity. An electrical current is passed from the conductive fluid, through the intermediate tissue, and into the target tissue to effect heating of the target tissue. The intermediate tissue is cooled by the conductive fluid. The conductive fluid will generally comprise an electrolytic solution such as saline, and the saline will preferably be chilled. Advantageously, by directing RF current between such a chilled electrolytic solution and a large cooled plate electrode, an intermediate collagenated tissue therebetween can be selectively raised above about 60° C., thereby inducing shrinkage. The tissue which is engaged directly by the cooled electrode and chilled electrolytic solution (on either side of the collagenated tissue) is preferably maintained below a maximum safe temperature of about 45° C.

In another aspect, the invention provides a method for shrinking a target tissue within a patient body. The target tissue is separated from a body cavity by an intermediate tissue. The method comprises introducing a conductive fluid and an insulating fluid into the cavity. These fluids are positioned within the cavity by orienting the patient. The conductive and insulating fluids will have differing densities, and the patient will be oriented so that the conductive fluid is disposed adjacent the target tissue, while the insulating fluid is disposed away from the target tissue. The target tissue can then be heated by passing an electrical current from the conductive fluid, through the intermediate tissue, and into the target tissue. The intermediate tissue can also be cooled by the conductive fluid. The conductive fluid will often comprise an electrolytic liquid such as saline, while the insulating fluid will typically comprise a gas such as air, carbon dioxide, or the like. By carefully controlling the volumes of these fluids within the body cavity, and by properly orienting the patient, gravity and the differing electrical properties of these contained fluids can be used to selectively transfer RF current from an electrode to a relatively large, controlled surface area of the body cavity without requiring the introduction of a large or mechanically complex electrode structure.

In another aspect, the present invention provides a method for treating urinary incontinence. The method comprises introducing a fluid into the bladder, and transmitting electrical current from the fluid, through the bladder wall, and into a pelvic support tissue so that the current heats and shrinks the pelvic support tissue and inhibits urinary incontinence. The bladder wall is cooled with the conductive fluid.

In another aspect, the present invention provides a system for shrinking a pelvic support tissue of a patient body. The pelvic support tissue is separated from a urinary bladder by a bladder wall. The system comprises a first probe having a proximal end and a distal end adapted for transurethral insertion into the bladder. A first electrode is disposed near the distal end, as is a fluid in-flow port. A sealing member is proximal of the in-flow port for sealing a conductive fluid within the bladder such that the first electrode is electrically coupled to the bladder wall by the conductive fluid. A second electrode is adapted for transmitting current to a tissue surface of the patient body without heating the tissue surface. A power source is coupled to the first and second electrodes to heat and shrink the pelvic support tissue. In many embodiments, the second electrode will comprise a cooled plate electrode of a vaginal probe, so that the endopelvic fascia can be selectively heated between the vagina and the conductive fluid within the bladder.

In another aspect, the present invention provides a system for shrinking a pelvic support tissue of a patient body. The pelvic support tissue is separated from a urinary bladder by a bladder wall. The system comprises a first probe having a proximal end, a distal end adapted for transurethral insertion into the bladder, and a first electrode near the distal end. A second probe has a proximal end, a distal end adapted for insertion into the vagina, and a second electrode near the distal end. A power source is coupled to the first and second electrodes to heat and shrink the pelvic support tissue. Generally, the first probe will also include a tordial balloon or other member for sealing around the circumference of the probe, thereby allowing saline or some other conductive fluid to be captured within the bladder. In some embodiments, in-flow and out-flow ports distal of the balloon may allow circulation of chilled saline or the like, enhancing the direct cooling of the bladder wall. One or more gas ports may also be provided distal of the balloon for introducing and/or controlling a volume of air, $CO_2$ or some other insulating gas, or such gasses may alternatively pass through the conductive fluid ports. By carefully controlling the volumes of air and saline within the bladder, and by orienting the patient so that the saline is only in contact with the bladder wall adjacent the endopelvic fascia, such a structure can provide both selective electrical conduction and cooling over a large, controlled surface of the bladder wall with very little mechanical complexity or trauma.

In general, the tissue contraction energy of the present invention can be applied as intermittent pulses of radio frequency (RF) electrical current transmitted between cooled electrodes. The electrodes will ideally be large, relatively flat plates having rounded edges, but may alternatively comprise a curved conductive surface of an inflatable balloon, or the like. These electrodes will preferably be oriented toward each other, and will generally be actively cooled while the electrodes are energized by a RF potential, and between RF pulses. Cooling will preferably also be provided both before and after the heating cycles, and needle mounted temperature sensors will ideally provide direct feedback of the tissue temperature so that selected treatment zone is heated to about 60° C. or more, while heating of the tissues adjacent the electrodes is limited to about 45° C. or less.

In one aspect, the present invention provides a method for heating and/or shrinking a target tissue within a patient body. The target tissue is separated from a tissue surface by an intermediate tissue. The method comprises coupling an electrode of a probe to the tissue surface and cooling the intermediate tissue with the probe. The electrode is intermittently energized to heat, and preferably to shrink, the target tissue through the cooled intermediate tissue. Typically, current is driven through the electrode for between about 10 and 50% of a heating session. For example, the electrode may be energized for 15 secs. and turned off for 15 secs. repeatedly during a heating session so that current is driven from the electrode for about 50% of the duty cycle.

In another aspect, the invention provides a system for shrinking a target tissue of a patient body. The system comprises a probe having a first electrode for electrically coupling the probe to the tissue surface. A second electrode can be coupled to the patient body, and a controller is coupled to the first and second electrodes. The controller is adapted to intermittently energize the electrodes with an RF current so that the electrodes heat and shrink the target tissue, often while minimizing collateral damage to tissues surrounding the target tissue. In many embodiments, The target tissue is separated from a tissue surface by an intermediate tissue. A cooling system may be disposed adjacent the electrode, so that the cooling system can maintain the intermediate tissue below a maximum safe temperature. Generally, the cooling system will cool both the first electrode and the intermediate tissue engaged by the electrode surface.

As described above, the energy to heat and selectively shrink the target collagenated support tissues will preferably be applied by conducting radio frequency (RF) electrical current through tissue disposed between large, cooled plate electrodes. These electrodes will preferably be sufficiently parallel to each other and in alignment so as to direct the current flux evenly throughout a target region of the target tissue. To maintain this alignment, the electrodes will generally be mechanically coupled to each other, ideally using a clamp structure which allows the target tissue to be compressed between the electrode surfaces. Compressing the tissues can enhance the uniformity of the heating, particularly when the tissue is compressed between the electrode surfaces so that the surfaces are separated by less than their widths. Cooling of the electrodes can limit heating of tissues adjacent the electrode surfaces to about 45° C. or less, even when the treatment zone between the electrodes is heated to about 60° C. or more so as to effect shrinkage.

In this aspect, the present invention provides a device for therapeutically heating tissue. The device comprises a first electrode having an electrode surface. A cooling system is thermally coupled to the first electrode. A second electrode is mechanically coupled to the first electrode. The second electrode has an electrode surface oriented toward the first electrode surface.

Generally, a clamp structure couples the electrodes and allows the tissues to be compressed between parallel electrode surfaces. The clamp structure will often be adapted to maintain the electrode surfaces in alignment to each other, and also to maintain the electrode surfaces sufficiently parallel so as to direct an even electrical current flux through a target region of the clamped tissue. At least one of the electrodes will preferably be mounted on a probe adapted for insertion into a patient body. The probe will ideally be adapted for noninvasive insertion into a body cavity through a body orifice. The clamp structure will preferably vary a separation distance between electrodes mounted on two such probes, and a temperature sensor will ideally be extendable into the target tissue to provide feedback on the heating process. The temperature sensor can be mounted on a needle which is retractably extendable from adjacent one of the electrodes toward the other, or the needle may protrude permanently so as to extend into the target tissue as the electrode surfaces are clamped together.

In another aspect, the present invention provides a method for selectively shrinking a target tissue. The method comprises clamping a target tissue between a plurality of electrode surfaces. The clamped target tissue is heated by transmitting a current flux between the electrode surfaces. At least one of the electrode surfaces is cooled to limit heating of intermediate tissue disposed between the at least one electrode and the target tissue.

According to another aspect of the invention, the energy can be in the form of focused ultrasound energy. Such ultrasound energy may be safely transmitted through an intermediate tissue at lower power densities so as to avoid and/or minimize collateral damage. By focusing the ultrasound energy at a target region which is smaller in cross section than the ultrasound energy transmitter, the power densities at the target region will be sufficiently high to increase the temperature of the target tissue. Preferably, the target tissue will be raised to a temperature of about 60° C. or more, while the intermediate tissue remains at or below a maximum safe temperature of about 45° C. A cooling system may actively cool the intermediate tissue.

Targeting flexibility is enhanced by using a phased array ultrasound transmitter. Such phased array transmitters will be particularly beneficial for selectively shrinking fascia, ligaments, and other thin support tissues of the body, particularly where those tissues are disposed roughly parallel to an accessible tissue surface. Focused ultrasound energy is particularly well suited for heating and shrinking the pelvic support tissues from a vaginal probe.

In this aspect, the present invention provides a method for heating a target tissue within a patient body. The target tissue is separated from a tissue surface by an intermediate tissue. The method comprises acoustically coupling an ultrasound transmitter to the tissue surface. The ultrasound energy is focused from the transmitter, through the intermediate tissue, and onto the target tissue so that the target tissue is therapeutically heated. Preferably, the focused ultrasound energy heats and shrinks a collagenated tissue. In the exemplary embodiment of the present method, the ultrasound transmitter is inserted into a vagina of the patient body to shrink an endopelvic support tissue so that incontinence is inhibited.

In another aspect, the present invention provides a system for heating a target tissue. The system comprises a probe having an ultrasound transmitter for focusing ultrasound energy through the intermediate tissue so as to heat the target tissue. Preferably, a temperature sensor is coupled to the probe and exposed to at least one of the intermediate tissue and the target tissue for sensing a tissue temperature. In many embodiments, a controller is coupled to the probe. The controller will generally be adapted to direct the ultrasound energy from the transmitter into the target tissue so as to heat the target tissue to about 60° C. or more. The controller will typically limit a temperature of the intermediate tissue to about 45° C. or less.

In yet another aspect, the present invention provides a method for selectively heating a predetermined target tissue. The target tissue is disposed adjacent another tissue, and the method comprises generating a temperature differential between the adjacent tissue and the target tissue. The target tissue is heated by conducting a heating electrical current into the target tissue after generating the temperature differential. The heating current is conducted so that the temperature differential urges the heating current from the adjacent tissue into the target tissue.

In a related aspect, the invention provides a system for selectively heating a predetermined target tissue. The target tissue is disposed adjacent another tissue, and the system comprises a probe having a surface oriented for engaging a tissue surface. A pre-cooler or a pre-heater is coupled to the probe surface so as to produce a temperature differential between the target tissue and the adjacent tissue. At least one tissue-heating electrode is couplable to the target tissue to conduct an electrical current into the tissues. The heating electrode defines a nominal current distribution when the current is conducted into the tissues and the tissues are at a uniform body temperature. The heating electrode produces a tailored current distribution when the current is conducted into the tissues and the tissues exhibit the temperature differential. The tailored current distribution results in less collateral damage to the adjacent tissue than the nominal current distribution when the target tissue is heated by the current to a treatment temperature.

In a final aspect, the invention provides a probe for selectively heating a target tissue. The target tissue is separated from a tissue surface by an intermediate tissue. The probe comprises a surface oriented for engaging the tissue surface. A pair of bi-polar electrodes are disposed along the probe surface. A cooling system is thermally coupled to the electrodes and to the probe surface, adjacent the electrodes, so as to cool the intermediate tissue.

DESCRIPTION OF THE SPECIFIC EMBODIMENTS

Figure 1:
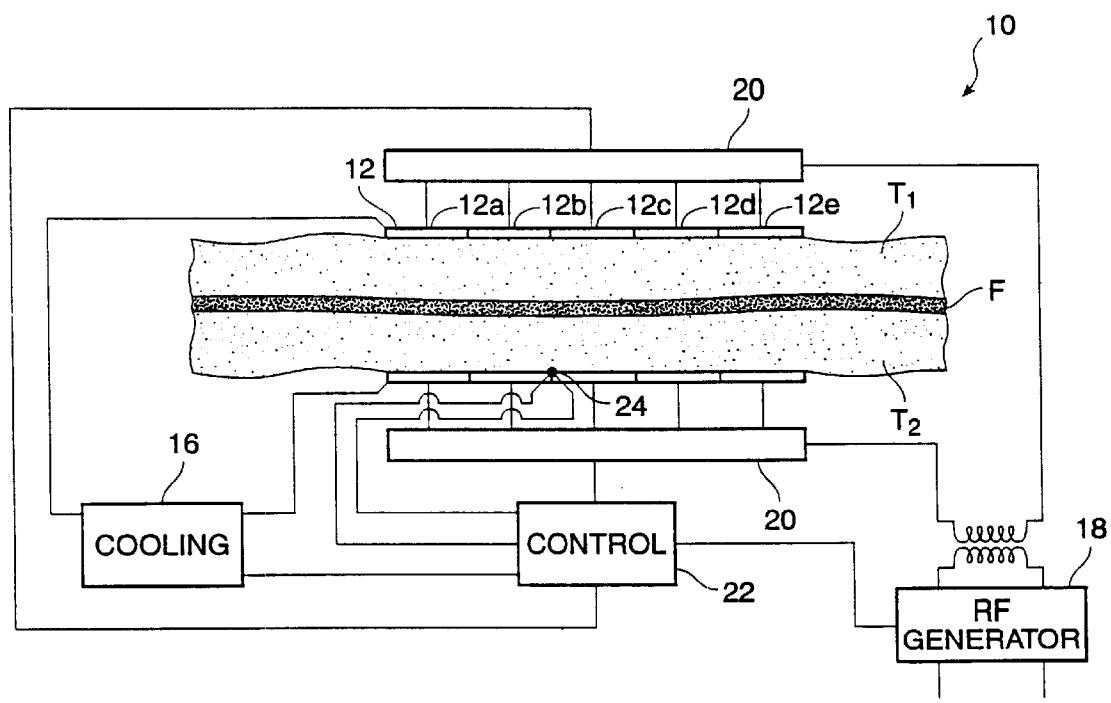
FIG. 1 is a schematic illustration of a system for heating and shrinking fascia disposed between adjacent tissue layers by heating the fascia between a pair of large, cooled, flat electrode arrays, according to the principles of the present invention.

The present invention optionally relies on inducing controlled shrinkage or contraction of a support tissue of the body, typically being a collagenated tissue such as fascia, ligament, or the like. For treatment of urinary incontinence, the tissue structure will be one that is responsible in some manner for control of urination, or for supporting a such a tissue. Exemplary tissue structures include the urethral wall, the bladder neck, the bladder, the urethra, bladder suspension ligaments, the sphincter, pelvic ligaments, pelvic floor muscles, fascia, and the like. Treatment of other conditions may be effected by selective shrinking of a wide variety of other tissues, including (but not limited to) the diaphragm, the abdominal wall, the breast supporting ligaments, the fascia and ligaments of the joints, the collagenated tissues of the skin, and the like. Related devices, methods, and system are also described in co-pending U.S. patent application Ser. No. 08/910,370 filed Aug. 13, 1997.

Tissue contraction results from controlled heating of the tissue by affecting the collagen molecules of the tissue. Contraction occurs as a result of heat-induced uncoiling and repositioning of the collagen â-pleated structure. By maintaining the times and temperatures set forth below, significant tissue contraction can be achieved without substantial collateral tissue damage.

The temperature of the target tissue structure will generally be raised to a value in the range from about 60° C. to 110° C., often being in the range from about 60° C. to 80° C., and will generally effect a shrinkage of the target tissue in at least one dimension of between about 20 and 50 percent. In many embodiments, heating energy will be applied for a period of from 30 seconds to 5 minutes. These heating times will vary with separation between the parallel plate electrodes, with a heat time of about 5 minutes often being appropriate for an electrode separation of about 4 cm. Shorter heat times may be used with smaller electrode separation distances.

The rise in temperature may be quite fast, although there will often be advantages in heating tissues more slowly, as this will allow more heat to be removed from tissues which are not targeted for therapy, thereby minimizing collateral damage. However, if too little heating energy is absorbed by the tissue, blood perfusion will transfer the heat away from the targeted tissue, so that the temperature will not rise sufficiently to effect therapy. Fortunately, fascia and other support tissues often have less blood flow than adjacent tissues and organs; this may help enhance the heating of fascia and minimize damage to the surrounding structures.

The total amount of energy delivered will depend in part on which tissue structure is being treated, how much tissue is disposed between the target tissue and the heating element, and the specific temperature and time selected for the protocol. The power delivered will often be in the range from 10 W to 200 W, usually being about 75 W. The temperature will usually not drop instantaneously when the heating energy stops, so that the tissue may remain at or near the therapy temperature for a time from about 10 seconds to about 2 minutes, and will often cool gradually back to body temperature.

While the remaining description is generally directed at devices and methods for treatment of urinary stress incontinence of a female patient, it will be appreciated that the present invention will find many other applications for selectively directing therapeutic heating energy into the tissues of a patient body for shrinking of tissues, for ablation of tissues and tumors, and the like.

FIG. 1 schematically illustrates a system 10 for shrinking a fascia F disposed between first and second adjacent tissues T1, T2. System 10 includes a pair of electrodes 12, 14 having large, substantially planar tissue engaging surfaces. Electrodes 12, 14 are aligned substantially parallel to each other with the fascia (and adjacent tissues) disposed therebetween.

The surfaces of electrodes 12, 14 which engage the tissue are cooled by a cooling system 16. The cooling system will typically include a conduit through the electrode for the circulation of a cooling fluid, but may optionally rely on thermoelectric cooling or the like. The temperature of the electrode surface may be regulated by varying the temperature or flow rate of the cooling fluid. Cooling may be provided through the use of an ice bath, by endothermic chemical reactions, by standard surgical room refrigeration mechanisms, or the like. Ideally, the cooling system cools an area which extends beyond the energized electrode surfaces to prevent any hot spots adjacent the tissue surface, and to maximize the heat removal from the tissue without chilling it to or below temperatures that irreversibly damage the tissue, such as might occur when freezing the tissue.

Each of the electrodes is separated into a plurality of electrode segments. For example, the electrode includes electrode segments 12a, 12b, 12c, 12d, and 12e, each of which is electrically isolated from the others. This allows the electrode segments to be individually energized.

Electrodes 12, 14 are energized by a radio frequency (RF) power source 18. Multiplexers 20 individually energize each electrode segment, typically varying the power or time each segment is energized to more nearly uniformly heat fascia F. A controller 22 will typically include a computer program which directs the application of cooling flow and RF power through electrodes 12, 14, ideally based at least in part on a temperature signal sensed by a temperature sensor 24. Temperature sensor 24 may sense the temperature of the electrode, the tissue at the tissue/electrode interface, the intermediate tissue, or may alternatively sense the temperature of the fascia itself. Alternatively, the controller may direct the cooling/heating therapy in an open loop manner using dosimetry.

Figure 2:
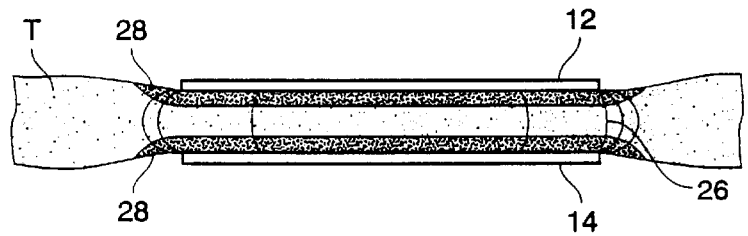
FIG. 2 schematically illustrates the even heating provided by a current flux between the large, cooled, flat electrode surfaces of the system of FIG. 1.

The use of large cooled plate electrodes to direct an even electrical current flux can be understood with reference to the simplified cross-sectional illustration of FIG. 2. In this example, RF power is applied uniformly across parallel plate electrodes 12, 14 to produce a current through tissue T. As the electrode surfaces are substantially planar, and as the length and width of the electrode surfaces are large compared to the separation between the electrodes, a current flux 26 is substantially uniform throughout that portion of the tissue which is disposed between the electrode surfaces. The flow of electrical current through the electrical resistance of the tissue causes the temperature of the tissue through which the current passes to rise. The use of a radio frequency current of relatively low voltage, preferably in the range from 100 kHz to 1 MHz, helps to avoid arcing and damage to tissue in direct contact with the electrodes.

Preliminary work in connection with the present invention has shown that fascia and other collagenated tissues which are heated to a temperature range of between about 60° C. and 140° C., often being in a range from about 60° C. to about 110° C., and preferably between about 60° C. and 80° C., will contract. In fact, unstressed fascia will shrink between about 30% and 50% when heated for a very short time, preferably from between about 0.5 seconds to 5 seconds. Such heating can easily be provided by conduction of RF currents through the tissue.

The uniform current flux provided by the large plate electrodes of the present invention will produce a substantially uniform heating of the tissue which passes that current. To selectively target a central portion of the tissue, in other words, to selectively heat a target portion of the tissue separated from electrodes 12, 14, the electrode surfaces are cooled. This cooling maintains a cooled tissue region 28 adjacent each electrode below a maximum safe tissue temperature, typically being below about 45° C. Even though heat generation throughout the gap between the electrodes is uniform, the temperature profile of the tissue between the electrodes can be controlled by removing heat through the electrode surfaces during heating.

Generally, sufficient heating can be provided by a current of between about 0.2 and 2.0 amps, ideally about 1.0 amp, and a maximum voltage of between about 30 and 100 volts rms., ideally being about 60 volts rms. The electrodes will often have a surface area of between about 5.0 and 200 cm$^2$, and the current density in the target tissue will often be between about 1 mA/cm$^2$ and 400 mA/cm$^2$, preferably being between about 5 mA/cm$^2$ and 50 mA/cm$^2$. This will provide a maximum power in the range from about 10 W to about 200 W, often being about 20 watts. Using such low power settings, if either electrode is lifted away from the engaged tissue, there will be no arcing. Instead, the current will simply stop. This highlights the difference between the electrical tissue heating of the present invention and known electrosurgical techniques.

The ideal geometry to provide a true one-dimensional temperature distribution would include large parallel plate electrodes having relatively minimal spacing therebetween. As tissues which are easily accessible for such structures are fairly limited, the present invention can also make use of electrode geometries which vary somewhat from this ideal, particularly through the use of array electrodes. In fact, the use of a single array electrode, in combination with a much larger, uncooled electrode pad may heat tissues disposed near the array, as will be described hereinbelow. Nonetheless, uniform heating is generally enhanced by providing electrode structures having tissue engaging surfaces which are as flat and/or as parallel as practical. Preferably, the parallel electrode surfaces will be separated by between about ⅓ and 5.0 times the width of the electrode surfaces (or of the smaller surface, if they are different).

Figure 2A:
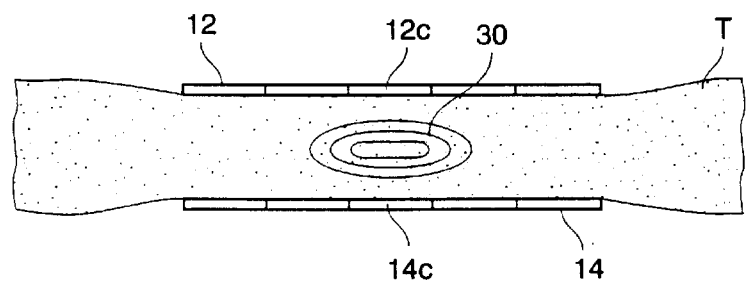
FIGS. 2A–2F schematically illustrate structures and methods for selectively energizing the electrode surface segments of the large, flat electrode arrays of the system of FIG. 1 to tailor the current flux throughout a target zone.
Figure 2B:
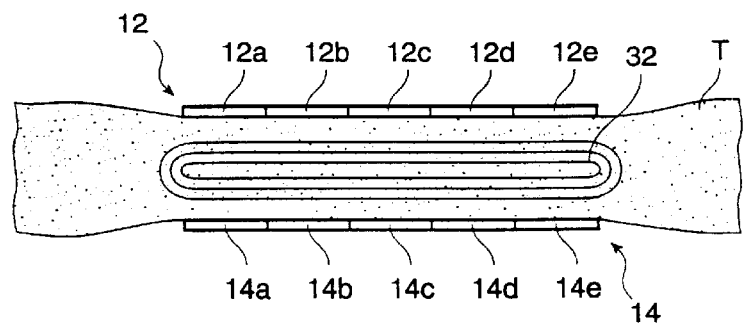

The use of an array electrode having multiple electrode segments can be understood with reference to FIGS. 2A–2D. FIG. 2A schematically illustrates the shape of a target zone which is heated by selectively energizing only electrode segments 12c and 14c of cooled electrodes 12 and 14. Once again, it should be understood that the temperature of target zone 32 (here illustrated schematically with isotemperature contour lines 30) is the result of uniform heating between the energized electrode segments, in combination with cooling of tissue T by the electrode surfaces. To expand the heated area laterally between the electrodes, electrode segments 12a, 12b, 12c . . . , and 14a, 14b, 14c . . . , can be energized, thereby heating an entire target zone 32 extending throughout tissue T between the electrodes.

Figure 2C:
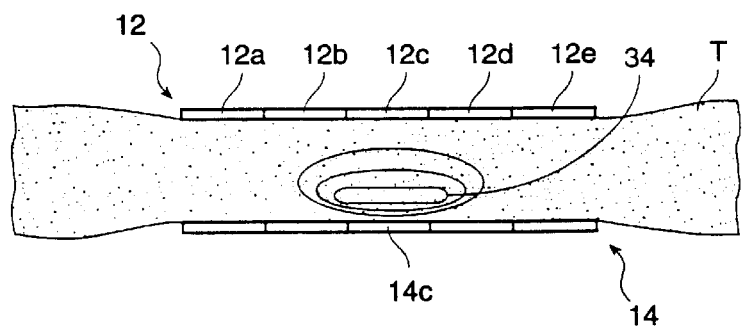

The use of array electrodes provides still further flexibility regarding the selective targeting of tissues between electrodes 12 and 14. As illustrated in FIG. 2C, selectively energizing a relatively large effective electrode surface by driving electrodes segments 12a, 12b, 12c, 12d, and 12e results in a low current flux which is widely disbursed throughout the tissue T engaged by electrode 12. By driving this same current through a relatively small effective electrode surface using only a single electrode surface segment 14c produces an offset target zone 34 which is laterally smaller than and much closer to electrode 14 than to electrode 12.

Figure 2D:
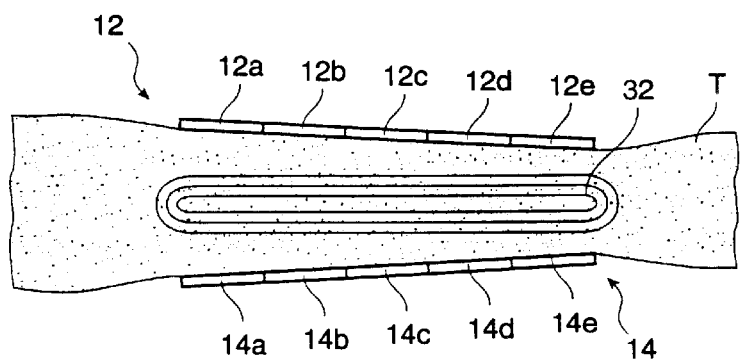

To compensate for electrode structures which are not exactly parallel, varying amounts of electrical current can be provided to the electrode segments. For example, a fairly uniform target zone 32 may be heated between angled electrodes by driving more current through relatively widely spaced electrode segments 12a, 14a, and driving less current through more tightly spaced electrode segments 12e, 14e, as illustrated in FIG. 2D. Alternatively, the same current may be driven between the segments, but for different intermittent duty cycles. It should be understood that these selective targeting mechanisms may be combined to target fascia and other tissues which are near one slanted electrode, or to selectively target only a portion of the tissues disposed between relatively large electrode arrays.

Figure 2E:
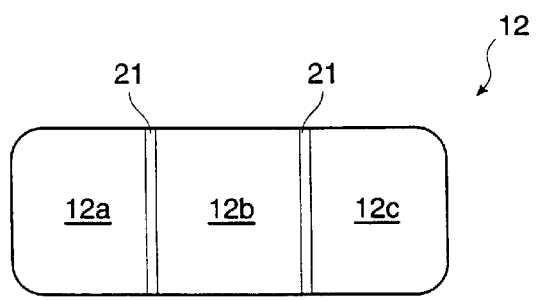
Figure 2F:
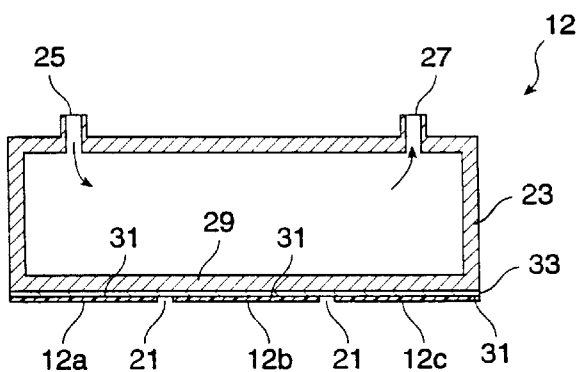

An exemplary structure for segmented, cooled electrode 12 is schematically illustrated in FIGS. 2E and F. Electrode 12 here comprises three electrode surface segments 12a, 12b, and 12c separated by insulating spaces 21. A plastic housing 23 defines a flow path between a cooling inflow port 25 and a cooling outflow port 27, while heat transfer between the cooling fluid and the electrode surface is enhanced by a thermally conductive front plate 29. Front plate 29 generally comprises a thermally conductive metal such as aluminum. Electrode surface segments 12a, 12b, and 12c may comprise surfaces of separated segments 31 of aluminum foil. Segments 31 may be electrically isolated and thermally coupled by a thin mylar insulation sheet 33 disposed between the segments and front plate 29.

The array electrode structures of the present invention will generally include a series of conductive surface segments which are aligned to define a substantially flat electrode surface. The electrode surface segments are separated by an electrically insulating material, with the insulation being much smaller in surface area than the conductive segments. Typically, there will be between 1.0 and 8.0 electrode segments, which are separated by a distance of between about 0.25 mm and 1.0 mm.

In some embodiments, the peripheral edges of the electrode segments may be rounded and/or covered by an insulating material to prevent concentrations of the electrical potential and injury to the engaged tissue surfaces.

It should also be understood that while the electrode arrays of the present invention are generally herein described with reference to a linear array geometry, the present invention also encompasses electrodes which are segmented into two-dimensional arrays. Where opposed sides of the tissue are accessible for relatively large array structures, such as along the exposed skin, or near the major cavities and orifices of the body, the electrode surfaces will preferably be separated by a gap which is less than a width (and length) of the electrodes.

In some embodiments, one electrode structure may be disposed within a large body cavity such as the rectum or vagina, while the other is placed in an adjacent cavity, or on the skin so that the region to be treated is between the electrode surfaces. In other embodiments, one or both electrodes may be inserted and positioned laparoscopically. It will often be desirable to clamp the tissue tightly between the electrodes to minimize the gap therebetween, and to promote efficient coupling of the electrode to the tissue.

Figure 3:
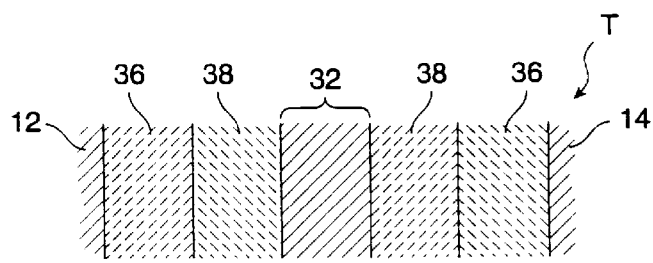
FIGS. 3–3E graphically illustrate a method for heating a target tissue between cooled electrodes, wherein the electrode surfaces cool the tissue before, during, and after radio frequency energy is applied.
Figure 3A:
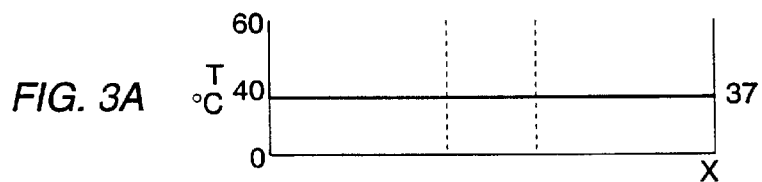
Figure 3B:
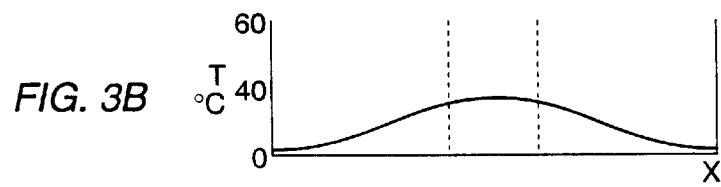
Figure 3C:
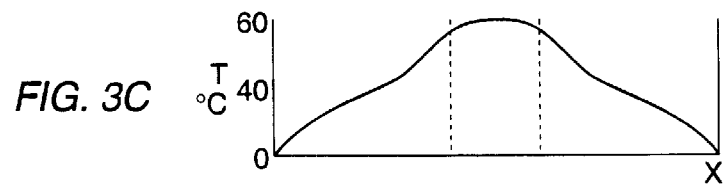
Figure 3D:
Figure 3E:
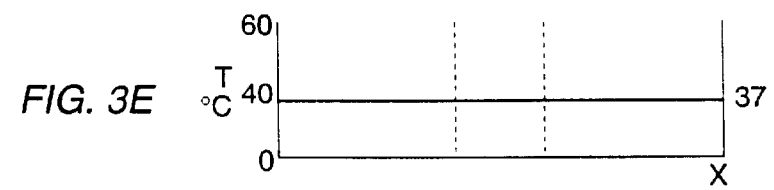

As can be understood with reference to FIGS. 3–3E, the tissue will preferably be cooled before and after energizing of the electrodes. FIG. 3 illustrates three distinct regions of tissue T disposed between electrodes 12 and 14. Target zone 32 will typically comprise fascia or some other collagenated tissue, while the surfaces of the electrodes engage an intermediate tissue 36 disposed on either side of the fascia.

It will generally be desirable to maintain the temperature of intermediate tissue 36 below a maximum safe tissue temperature to prevent injury to this intermediate tissue, the maximum safe tissue temperature typically being about 45° C. To effect shrinkage of fascia, target zone 32 will typically be heated to a temperature above about 60° C., and often to a temperature at or above 70° C.

There will often be a region of stunned tissue 38 disposed between the safely cooled intermediate tissue 36 and the target zone 32. This stunned tissue will typically be heated in the range from about 45° C. to about 60° C., and may therefore undergo some limited injury during the treatment process. As a result, it is generally desirable to minimize the time this tissue is at an elevated temperature, as well as the amount of stunned tissue.

As illustrated in FIG. 3A, prior to application of cooling or heating energy, the temperature profile of tissue T along an axis X between electrodes 12 and 14 is substantially uniform at body temperature (approximately 37° C.). The tissue will preferably be pre-cooled by the surfaces of electrodes 12, 14, generally using an electrode surface temperature of at or above 0° C. Pre-cooling will substantially decrease the temperature of intermediate tissues 36, and will preferably at least partially decrease the temperature of stunned tissue 38. At least a portion of the target zone remains at or near the initial body temperature, as illustrated in FIG. 3B. Pre-cooling time will often depend on electrode separation and tissue heat diffusivity.

As will be explained in more detail regarding FIGS. 12–12L, pre-cooling (and/or pre-heating) of selective portions of the tissue engaged by a cooled electrode can alter the electrical current densities within tissues so as to provide selective, localized heating. Referring to FIG. 3B, intermediate tissue 36 exhibits a substantial temperature differential as compared to target tissue 32. As a result of this temperature differential, the electrical impedance of an immediate tissue 36 has been enhanced relative to target tissue 32. This does not necessarily mean that the impedance of the intermediate tissue is now greater than that of the target tissue (although this will often be the case). Regardless, as compared to the tissues at uniform body temperature, the temperature differential between the target and intermediate tissues can now be used to help enhance selective heating of the target tissue while minimizing collateral damage to the adjacent tissue.

Once the tissue has been pre-cooled, the RF current is directed through the tissue between the electrodes to heat the tissue. A temperature sensor can be placed at the center of target zone 32 to help determine when the pre-cooling has been applied for the proper time to initiate RF heating. The current flux applies a fairly uniform heating throughout the tissue between the electrodes, and the electrode surfaces are often cooled throughout the heating process. As target zone 32 has the highest temperature upon initiation of the heating cycle, and as the target zone is farthest from the cooled electrodes, a relatively small amount of heat flows from the target zone into the cooled electrodes, and the target zone is heated to a significantly higher temperature than intermediate tissue 36.

Heat is applied until the target zone is at or above a treatment temperature, typically resulting in a temperature distribution such as that illustrated in FIG. 3C. To minimize collateral damage to the adjacent tissues 36 and stunned tissue 38, the cooling system continues to circulate cold fluid through the electrode, and to remove heat from the tissue, after the heating radio frequency energy is halted. When substantially the entire tissue is below the maximum safe tissue temperature (as in FIG. 3D), cooling can be halted, and the tissue can be allowed to return to standard body temperature, as illustrated in FIG. 3E.

Optionally, RF current may be driven between the two cooled plate electrodes using intermittent pulses of excitation. As used herein, intermittent or pulsed excitation encompasses cyclically increasing and decreasing delivered power, including cyclical variations in RMS power provided by amplitude modulation, waveform shape modulation, pulse width modulation, or the like. Such intermittent excitation will preferably provide no more than about 25% of the RMS power of the pulses during the intervals between pulses. Preferably, the electrodes will be energized for between about 10 and 50% of a total heating session. For example, electrodes 12 and 14 may be energized for 15 secs. and then turned off for 15 secs. and then cycled on and off again repeatedly until the target tissue has been heated sufficiently to effect the desired shrinkage. Preferably, the electrode surfaces (and the surrounding probe structure which engages the tissue) will be cooled throughout the on/off cycles of the heating sessions.

The therapeutic heating and cooling provided by the electrodes of the present invention will often be verified and/or controlled by sensing the temperature of the target tissue and the adjacent tissue directly. Such temperature sensing may be provided using a needle containing two temperature sensors: one at the tip to be positioned at the center of the treatment zone, and the second along the shaft of the needle so as to be positioned at the edge of the desired protection zone. In other words, the second sensor will be placed along the border between the intermediate tissue and the target tissue, typically somewhere along stunned tissue 38. The temperature sensors will preferably sense the tissue temperature during the intervals between pulses to minimize errors induced by the heating RF current flux in the surrounding tissue. The temperature sensors may comprise thermistors, thermocouples, or the like.

The temperature sensing needle may be affixed to or advancable from a probe supporting the electrode adjacent to or between the electrode segments. Alternatively, two or more needles may be used. Typically, controller 22 will provide signals to cooling system 16 and the electrodes so that the electrodes chill the engaged tissue continually while the RF current is pulsed to increase the temperature of the treatment zone incrementally, ideally in a step-wise manner, until it reaches a temperature of 60° C. or more, while at the same time limiting heating of the intermediate tissue to 45° C. or less per the feedback from the needles.

In alternative embodiments, pre-chilling time, the duration of the heat, the lengths of the heating intervals (and the time between heating intervals) during intermittent heating, and the radio frequency heating current may be controlled without having direct feedback by using dosimetry. Where the thermal properties of these tissues are sufficiently predictable, the effect of treatment can be estimated from previous measurements.

Figure 4:
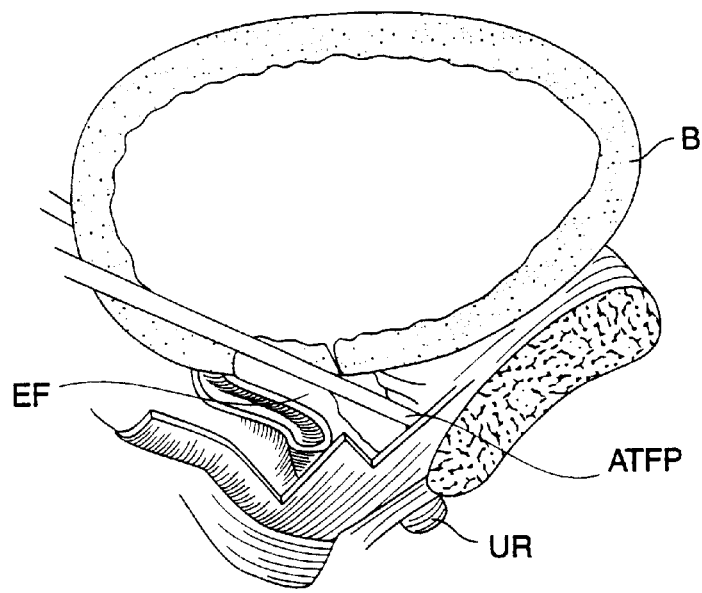
FIG. 4 is a cut-away view illustrating pelvic support structures which can be targeted for non-invasive selective contraction using the methods of the present invention.

The pelvic support tissues which generally maintain the position of the urinary bladder B are illustrated in FIG. 4. Of particular importance for the method of the present invention, endopelvic fascia EF defines a hammock-like structure which extends between the arcus tendineus fascia pelvis ATFP. These latter structures extend between the anterior and posterior portions of the pelvic bone, so that the endopelvic fascia EF largely defines the pelvic floor.

In women with urinary stress incontinence due to bladder neck hypermobility, the bladder has typically dropped between about 1.0 cm and 1.5 cm (or more) below its nominal position. This condition is typically due to weakening of the pelvic support structures, including the endopelvic fascia, the arcus tendineus fascia pelvis, and the surrounding ligaments and muscles, often as the result of bearing children.

When a woman with urinary stress incontinence sneezes, coughs, laughs, or exercises, the abdominal pressure often increases momentarily. Such pressure pulses force the bladder to descend still further, shortening the urethra UR and momentarily opening the urinary sphincter.

Figure 4A:
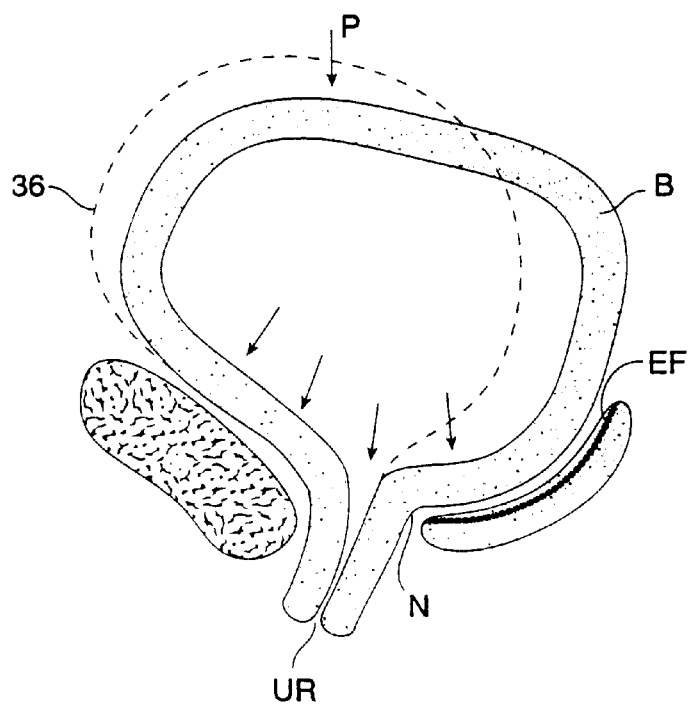
FIGS. 4A–4C illustrate contraction and reinforcing of the pelvic support tissues of FIG. 4 as a therapies for female urinary incontinence.
Figure 4B:
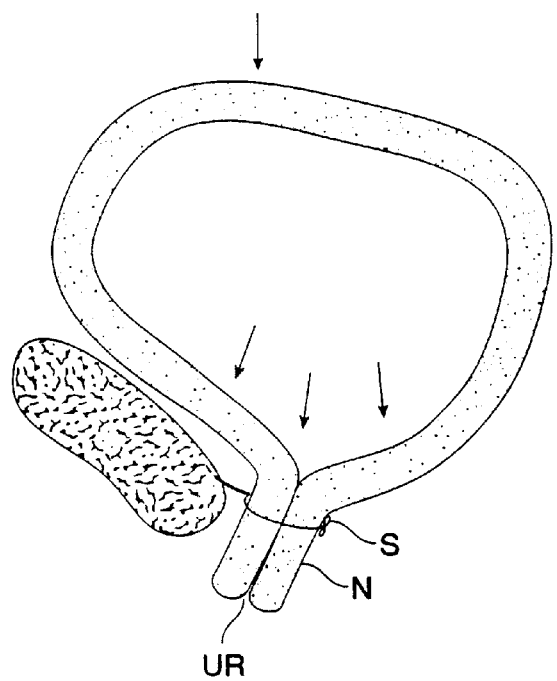
Figure 4C:
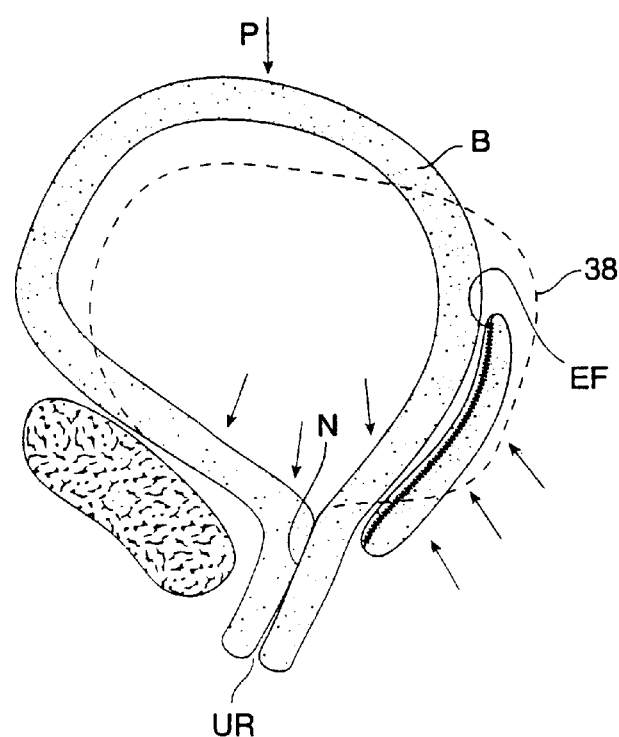

As can be most clearly understood with reference to FIGS. 4A–4C, the present invention generally provides a therapy which applies gentle heating to shrink the length of the support tissues and return bladder B to its nominal position. Advantageously, the bladder is still supported by the fascia, muscles, ligaments, and tendons of the body. Using gentle resistive heating between bipolar electrodes, the endopelvic fascia EF and arcus tendineus fascia pelvis ATFP are controllably contracted to shrink them and re-elevate the bladder toward its original position.

Referring now to FIG. 4A, bladder B can be seen to have dropped from its nominal position (shown in phantom by outline 36). While endopelvic fascia EF still supports bladder B to maintain continence when the patient is at rest, a momentary pressure pulse P opens the bladder neck N, resulting in a release through urethra UR.

A known treatment for urinary stress incontinence relies on sutures S to hold bladder neck N closed so as to prevent inadvertent voiding, as seen in FIG. 4B. Sutures S may be attached to bone anchors affixed to the pubic bone, ligaments higher in the pelvic region, or the like. In any case, loose sutures provide insufficient support of the bladder neck N and fail to overcome urinary stress incontinence, while overtightening of sutures S may make normal urination difficult and/or impossible.

As shown in FIG. 4C, by selectively contracting the natural pelvic support tissues, bladder B can be elevated from its lowered position (shown by lowered outline 38). A pressure pulse P is resisted in part by endopelvic fascia EF, which supports the lower portion of the bladder and helps maintain the bladder neck in a closed configuration. In fact, fine tuning of the support provided by the endopelvic fascia is possible through selective contraction of the anterior portion of the endopelvic fascia to close the bladder neck and raise bladder B upward. Alternatively, lateral repositioning of bladder B to a more forward position may be affected by selectively contracting the dorsal portion of endopelvic fascia EF. Hence, the therapy of the present invention may be tailored to the particular elongation exhibited by a patient's pelvic support tissues.

As is more fully explained in published PCT Patent Application Publication No. WO 97/20191, a wide variety of alternative conditions may also be treated using the methods of the present invention. In particular, selective shrinkage of fascia may effectively treat cystocele, hiatal, and inguinal hernias, and may even be used in cosmetic procedures such as abdominoplasty (through selectively shrinking of the abdominal wall), to remove wrinkles by shrinking the collagenated skin tissues, or to lift sagging breasts by shrinking their support ligaments.

Figure 5:
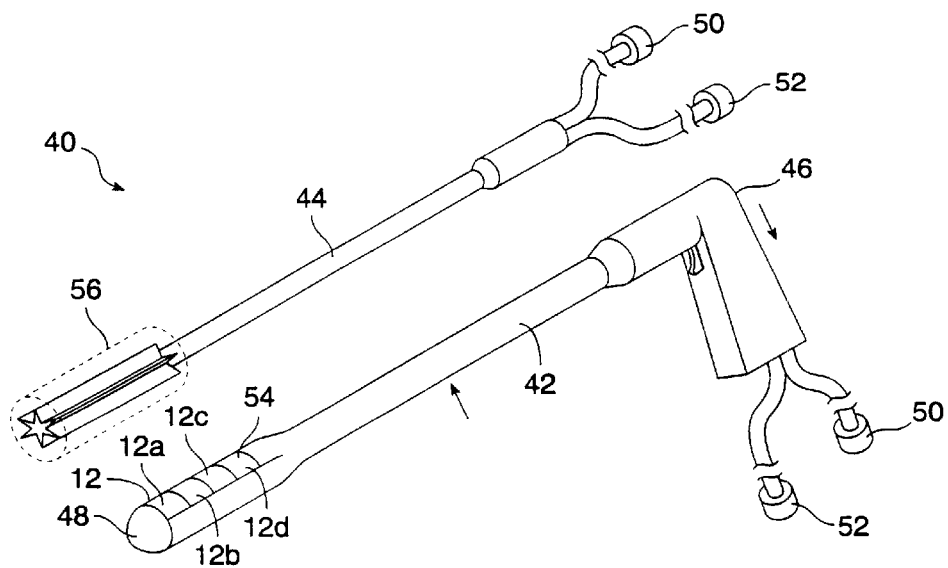
FIG. 5 is a perspective view of a system for treating female urinary incontinence by selectively shrinking the endopelvic fascia, according to the principles of the present invention.

A system for selectively shrinking the endopelvic fascia is illustrated in FIG. 5. System 40 includes a vaginal probe 42 and a bladder probe 44. Vaginal probe 42 has a proximal end 46 and a distal end 48. Electrode 12 (including segments 12a, 12b, 12c, and 12d) is mounted near the distal end of the probe. Vaginal probe 42 will typically have a diameter of between about 2 and 4 cm, and will often have a shaft length of between about 6 and 12 cm. An electrical coupling 50 is coupleable to an RF power supply, and optionally to an external control processor. Alternatively, a controller may be integrated into the probe itself. A fluid coupling 52 provides attachment to a cooling fluid system. Cooling fluid may be recycled through the probe, so that more than one fluid couplers may be provided.

The segments of electrode 12 are quite close to each other, and preferably define a substantially flat electrode surface 54. The cooling fluid flows immediately below this surface, the surface material preferably being both thermally and electrically conductive. Ideally, surface 54 is as large as the tissue region to be treated, and a thermocouple or other temperature sensor may be mounted adjacent the surface for engaging the tissue surface and measuring the temperature of the engaged tissue.

Figure 6:
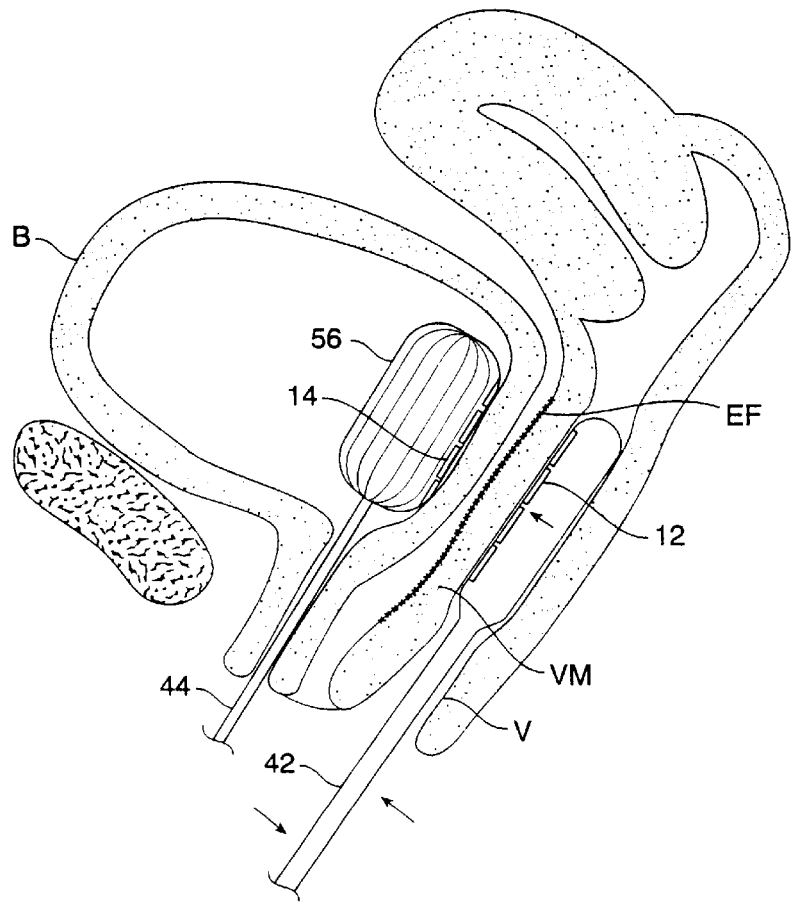
FIG. 6 is a cross-sectional view illustrating a method for using the system of FIG. 5 to treat female urinary incontinence.

Urethral probe 44 includes a balloon 56 supporting a deployable electrode surface. This allows the use of a larger electrode surface than could normally be inserted through the urethra, by expanding the balloon structure within the bladder as illustrated in FIG. 6. Alternatively, a narrower cylindrical electrode might be used which engages the surrounding urethra, the urethral electrode optionally being separated into more than one segment along the length and/or around the circumference of the probe shaft. Radio frequency current will divert from such a tightly curved surface and heat the nearby tissue. The electrode can again be chilled to protect the urethral lining from thermal damage. Probe 44 may include a temperature measuring device to ensure that the temperature of the intermediate tissue does not rise above 45° C. adjacent the electrode.

As illustrated in FIG. 6, the endopelvic fascia will preferably be disposed between the electrodes of the urethral probe 44 and vaginal probe 42 when the vaginal probe is levered to the right or the left side of the pelvis by the physician. Balloon 56 of urethral probe 44 is here illustrated in its expanded configuration, thereby maximizing a surface area of electrode 14, and also minimizing its curvature (or in other words, minimizing the radius of curvature of the electrode surface). Preferably, cooled fluid recirculating through balloon 56 will cool electrode 14, so that cooled electrodes 12, 14 will selectively heat the endopelvic fascia EF without damaging the delicate vaginal wall VW or the bladder wall.

Urethral probe 44 and vaginal probe 42 may optionally be coupleable to each other to facilitate aligning the probes on either side of the target tissue, either mechanically or by some remote sensing system. For example, one of the probes may include an ultrasound transducer, thereby facilitating alignment of the electrode surfaces and identification of the target tissue. Alternatively, the proximal ends of the probes may attach together to align the electrodes and/or clamp the target tissue between the probes.

In some embodiments, cooled fluid may be recirculated through bladder B so as to cool the bladder wall without conducting electrical heating current from within the bladder. Optionally, such a cooling fluid flow may be provided within balloon 56. Alternatively, the cooling fluid flow could be recirculated within the bladder cavity in direct contact with the bladder wall. Such a cooling flow might be provided with a two lumen (an inflow lumen and an outflow lumen) catheter, the catheter optionally having a sealing member (such as a toroidal balloon around the catheter) to contain the cooling fluid within the bladder once the catheter is inserted through the urethra. Such a cooling flow can help limit the depth of tissue heating when using a monopolar transvaginal probe, or when using a bipolar probe such as those described in FIGS. 12–12L.

Figure 7:
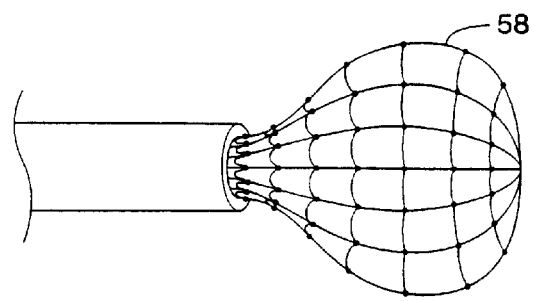
FIG. 7 illustrates an alternative bladder electrode structure for use in the method of FIG. 6.

Referring now to FIG. 7, a mesh electrode 58 may be unfurled within the bladder in place of urethral probe 44. Mesh electrode 58 preferably comprises a highly flexible conductive element, optionally being formed of a shape memory alloy such as Nitinol™. The bladder may be filled with an electrically non-conductive fluid such as distilled water during the therapy, so that little or no RF current would flow into the bladder wall beyond the contact region between the electrode and the bladder. To limit heating of tissues which are disposed above the bladder, an upper portion 58 of the mesh structure may be masked off electrically from the energized mesh surface of the lower portion.

Figure 8A:
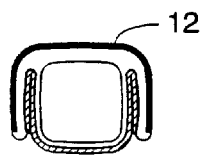
FIGS. 8A and 8B illustrate an alternative vaginal probe having a balloon deployable electrode for use in the method of FIG. 6.
Figure 8B:
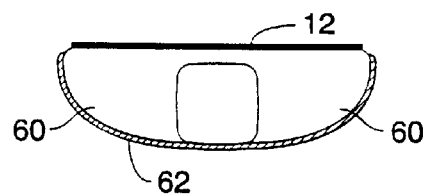

FIGS. 8A and 8B illustrate an optional deployable electrode support structure for use with vaginal probe 42. Electrode 12 can be collapsed into a narrow configuration for insertion and positioning within the vaginal cavity, as illustrated in FIG. 8A. Once electrode 12 is positioned adjacent to the target tissue, electrode 12 can be expanded by inflating lateral balloon 60 so that the deployed electrode assumes a substantially planar configuration. A cooling fluid may be recirculated through lateral balloon 60 to cool the electrode 12, and a thermally insulating layer 62 can help to minimize heat transfer from the adjacent tissues.

Figure 9:
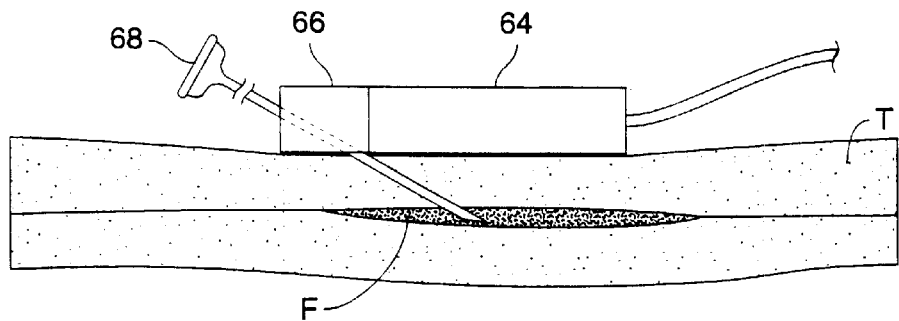
FIG. 9 is a cross-sectional view illustrating a structure and a method for ultrasonically positioning a temperature sensor within a target tissue.

Referring now to FIG. 9, the tissue shrinking system of the present invention may also include an ultrasonic transducer 64 for positioning one or both electrodes relative to fascia F. Transducer 64 will preferably include a plastic transducer material such as PVDF (polyvinyladine fluoride) or PZT-5A (lead zirconate titanate). Transducer 64 may be incorporated into the probes of the present invention, thereby allowing the relative positions and angle between the electrode surfaces to be measured directly. Alternatively, transducer 64 may be positioned adjacent to fascia F, and a mark may be drawn upon the exposed skin (or other tissue surface) adjacent the fascia for subsequent positioning of a probe.

Transducer 64 optionally includes a needle guide 66 for insertion of a biopsy needle 68 through the view of the transducer and into the fascia. A thermocouple or other temperature sensing element may then be deployed using or in place of the biopsy needle.

Figure 10:
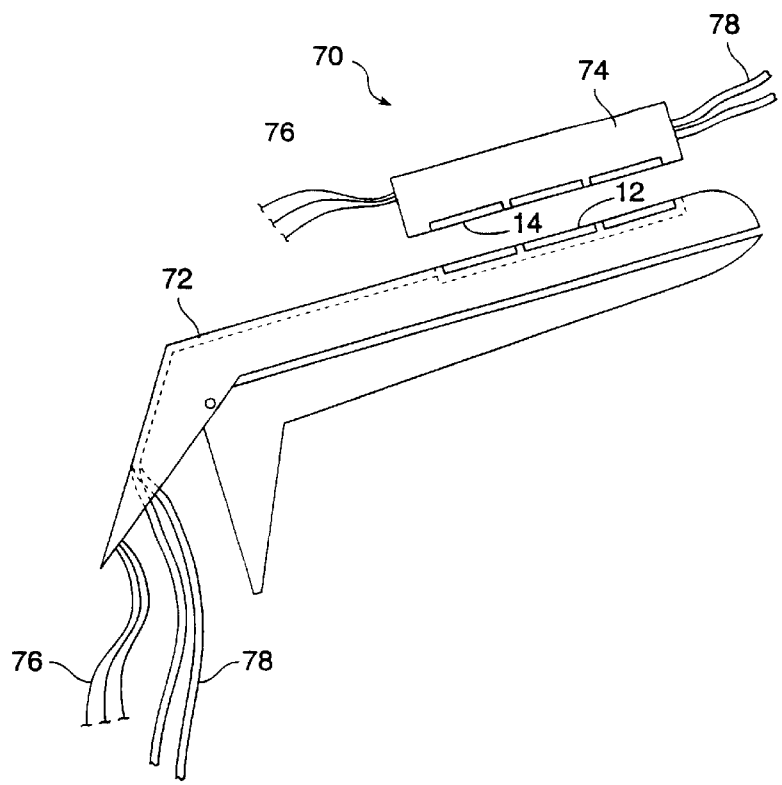
FIG. 10 illustrates an alternative system for selectively shrinking fascia through intermediate tissues, according to the principles of the present invention.

Referring now to FIG. 10, an alternative tissue shrinking system 70 includes an electrode 12 mounted on a speculum 72. Speculum 72 may be used to manually position electrode 12 within the vagina (or another body orifice), while an external applicator 74 is positioned against the skin to clamp the target tissue between electrode 14 and electrode 12. The speculum and external applicator 74 may be manually manipulated to clamp the target tissue between these structures, while electrical leads 76 and cooling fluid conduits 78 couple the probe and applicator to the remaining system components.

Figure 11:
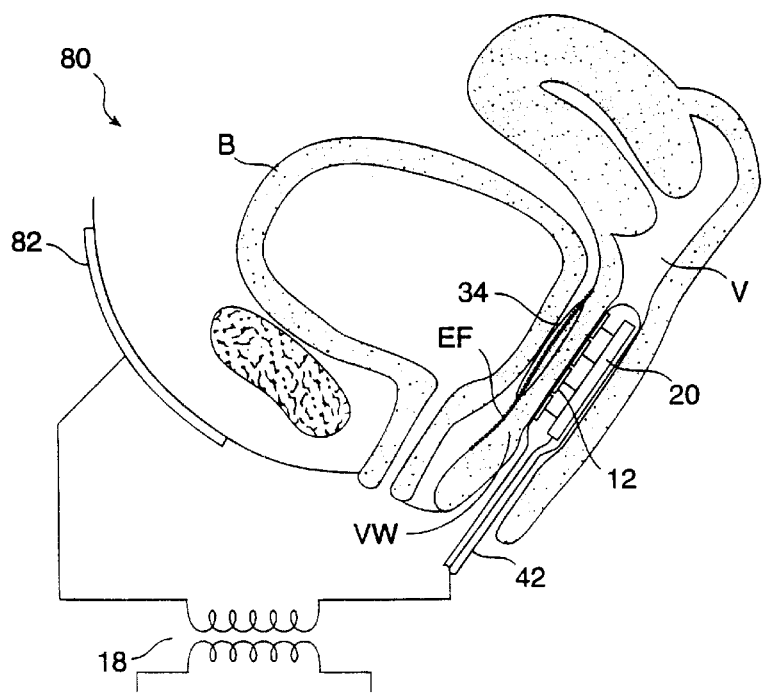
FIG. 11 schematically illustrates an alternative method for selectively shrinking endopelvic fascia using a vaginal probe having a cooled electrode array and a return electrode.

As described above regarding FIG. 2C, the use of bipolar electrodes of differing sizes allows the selective targeting of tissues. Specifically, heating will be concentrated near the smaller electrode surface. By using one electrode surface which is much larger than the other, the current density adjacent the large electrode will remain so low that little tissue heating is produced at that site, so that the very large electrode surface need not be cooled. FIG. 11 schematically illustrates a single probe heating system 80 which takes advantage of this mechanism to selectively heat fascia near a single probe.

In single probe system 80, offset target zone 34 is heated by RF energy selectively directed through the segments of electrode 12. The vaginal wall VW disposed between vaginal probe 42 and endopelvic fascia EF is protected by cooling the surface of electrode 12, as described above. Bladder B (and the other tissues opposite endopelvic fascia EF relative to vaginal probe 42) are heated significantly less than endopelvic fascia EF due to the divergence of the current as it travels away from electrode 12 and towards electrode pad 82, which may optionally be disposed on the abdomen, back, or thigh. Optionally, cooling water may be circulated through bladder B to further protect these tissues by direct cooling and by raising the impedance of the cooled tissue to lower heating (particularly when the bladder wall is pre-chilled prior to heating). Multiplexer 20 selectively energizes the electrode segments for differing amounts of time and/or with differing power to help tailor the temperature profile of offset target zone 34 about endopelvic fascia EF for selective uniform heating with minimal collateral damage. Various treatment regimes with alternating heating and cooling cycles can help to focus the heat therapy on the desired tissues. Multiplexer 20 may be disposed outside of the body in a proximal housing, in a separate control unit housing, or the like. The multiplexer can provide electrode segment drive control, optionally with switches for each electrode segment.

Figure 12:
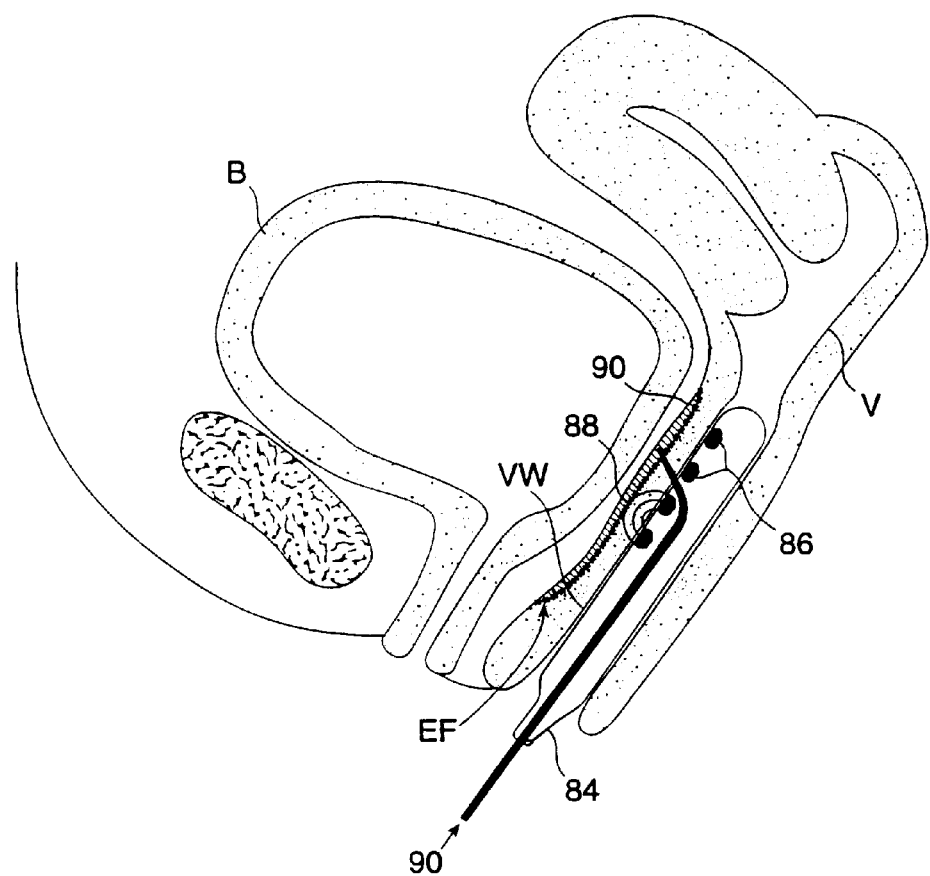
FIG. 12 schematically illustrates cooled bipolar probe and a method for its use to selectively shrink endopelvic fascia by applying a bipolar potential between electrode segments of the probe, the method including electrically insulating a surface of the endopelvic fascia opposite the probe to limit the depth of heating.

Referring now to FIG. 12, a cooled bipolar probe 84 includes many of the structures and features described above, but here includes a series of bipolar electrodes 86. Bi-polar electrodes 86 will preferably be cooled, and cooling surfaces may also be disposed between the separated electrodes. Bi-polar electrodes 86 may optionally be formed as parallel cylindrical structures separated by a predetermined spacing to help direct a bipolar current flux 88 through tissue which lies within a particular treatment distance of probe 84.

The depth of penetration of the bipolar energy can be controlled by the spacing, size, and shape (i.e., the radius of curvature) of the electrode structures. The tissues distant from the cooled electrodes can be heated to a greater extent than the tissues directly engaged by the electrodes, and will be cooled to a lesser extent by the cooled electrodes and other cooling surfaces of bipolar probe 84. The tissues close to the electrodes can be protected from burning to a greater extent, and will also be cooled directly and actively. Therefore, a controlled regimen of timed pre-cooling and then heating is used to selectively raise the temperature of endopelvic fascia EF (or any other target tissue), while the vaginal mucosa adjacent probe 84 is protected by the cooled probe. Tissues at depths greater than the endopelvic fascia will generally be protected by the dissipation of bipolar current 88.

Since radio frequency heating generally relies on conduction of electricity through the tissue, one additional mechanism for protecting the tissues at depths greater than the target area would be to inject an insulating fluid 90 into the space surrounding the vaginal wall on the far side of endopelvic fascia EF. Insulating fluid 90 may optionally comprise a gas such as $CO_2$, or may alternatively comprise a liquid such as isotonic Dextran™ in water. Insulating fluid 90 will electrically insulate the adjacent organs and prevent heating of tissues that might otherwise be in contact with the vaginal fascial outer lining. Insulating fluid 90 is here injected using a small needle incorporated into bipolar probe 84, the needle preferably being 22 ga or smaller.

Figure 12A:
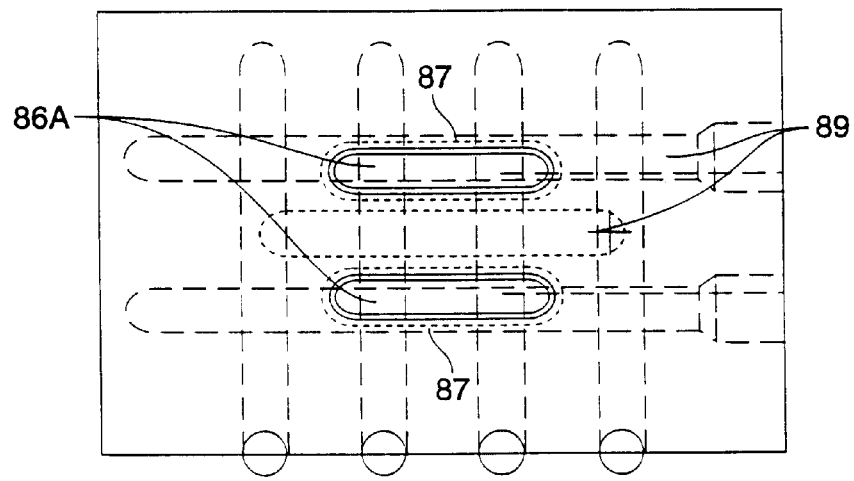
FIGS. 12A–L illustrate a variety of cooled bi-polar probes and methods for their use to selectively heat tissues separated from the probe by an adjacent tissue.
Figure 12B:
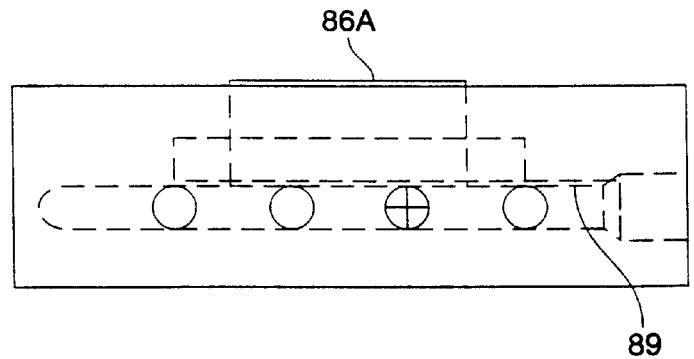
Figure 12C:
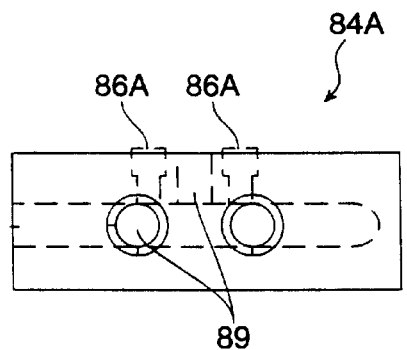
Figure 12D:
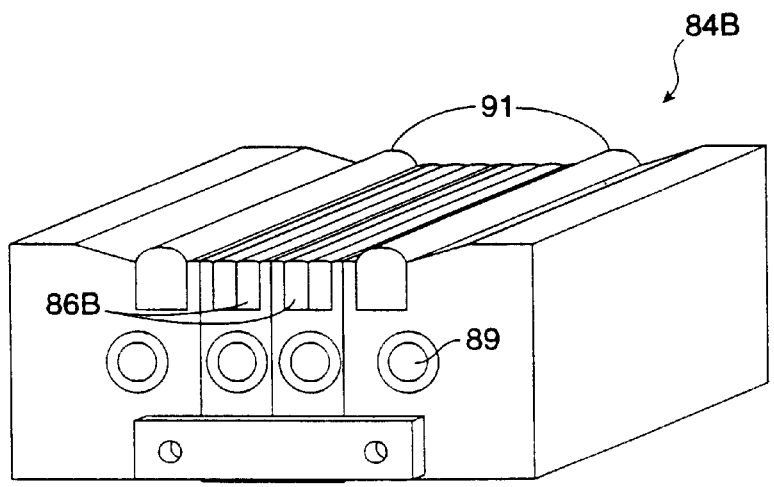
Figure 12E:
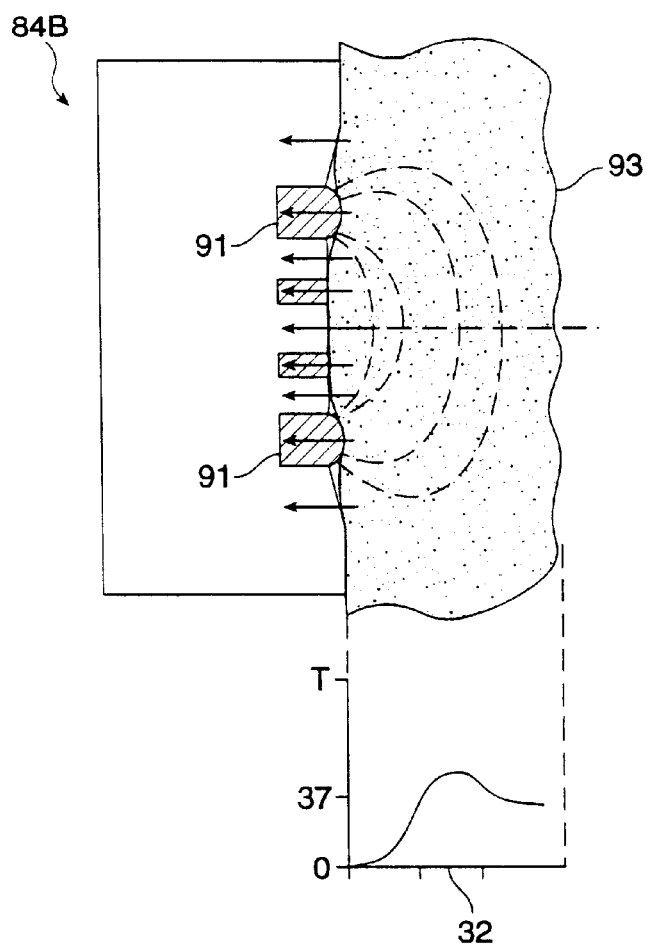
Figure 12F:
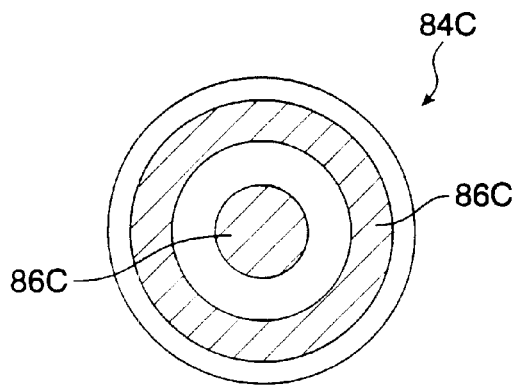
Figure 12G:
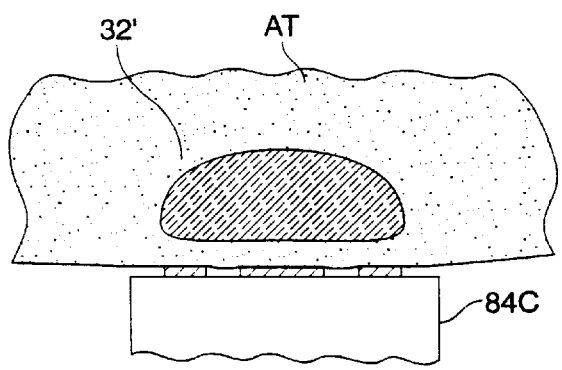
Figure 12H:
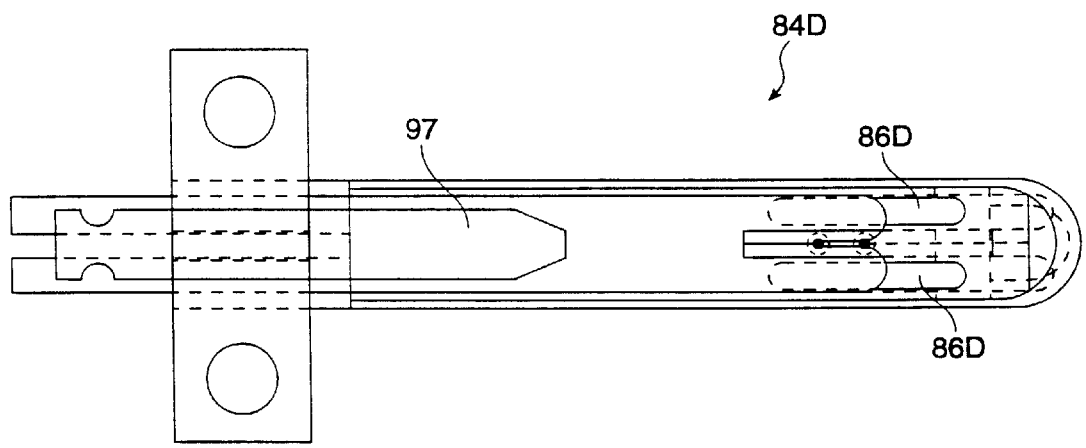
Figure 12I:
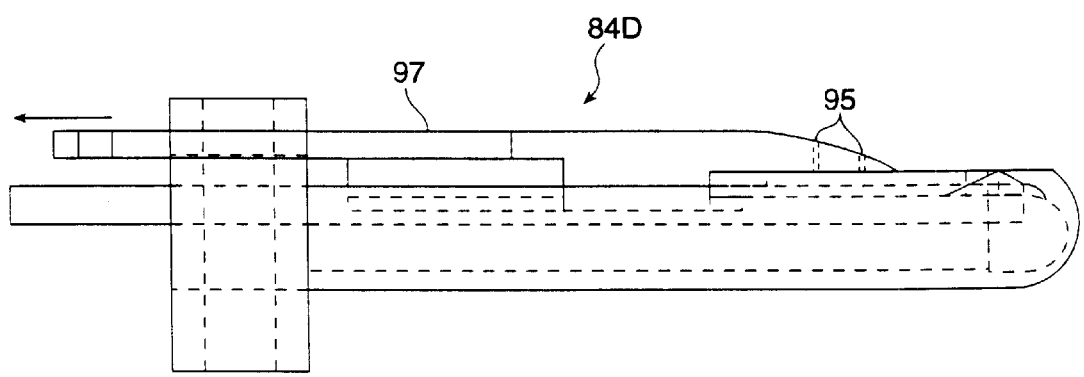
Figure 12J:
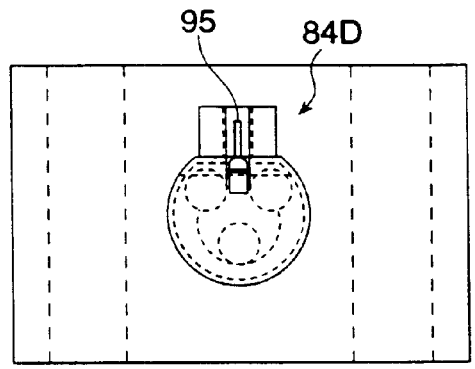
Figure 12K:
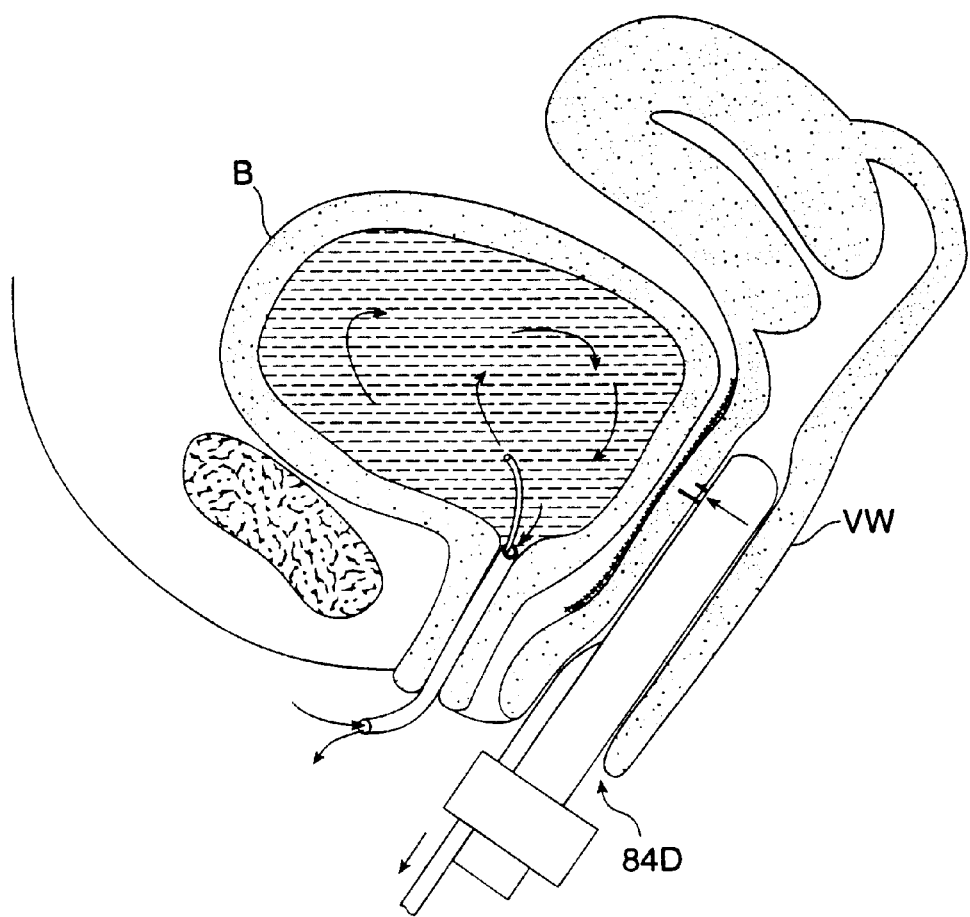
Figure 12L:
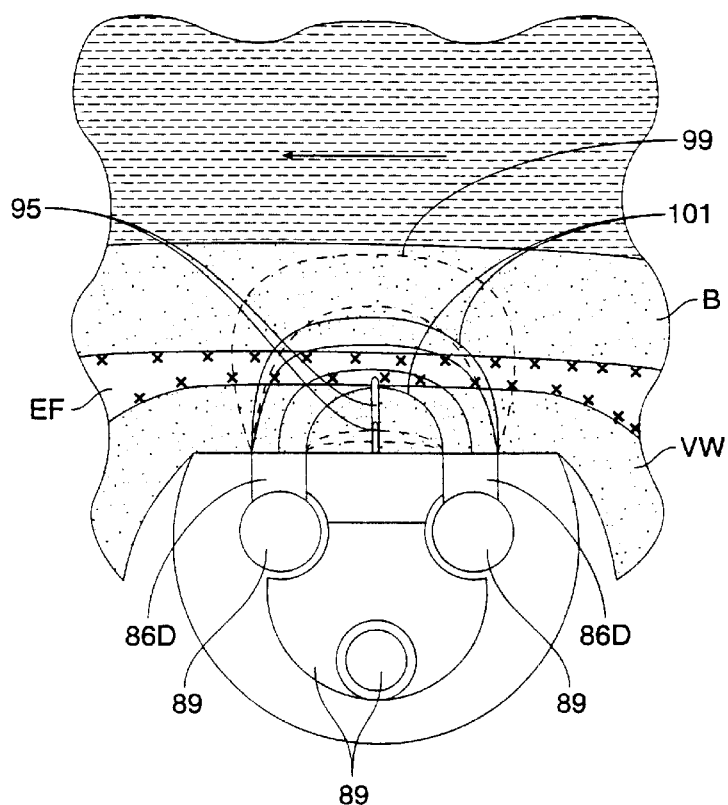

A variety of alternative cooled bipolar probe structures are illustrated in FIGS. 12A–L. Referring first to FIGS. 12A–C, a simple cooled bi-polar probe 84A includes a pair of bi-polar electrodes 86A which are insulated from a probe body by inserts 87. The probe body includes a cooling channel system 89 which cools electrodes 86A and at least a portion of the surrounding surface of the probe body. Surprisingly, by properly spacing electrodes 86A (typically by a distance from about ⅓ to about 5 times the least width of the electrodes, and preferably by a distance from about ½ to about 2 times the least electrode width), and by properly cooling the tissue surface before initiating RF heating; arcing, charring and excessive collateral damage to the engaged tissue surface can be avoided even when using electrodes having substantially planer electrode surfaces without radiused edges. Rounding the corners of electrodes 86A may optionally still further minimize concentrations of electrical current. In many embodiments, cooling channel system 89 will include channels adjacent to and/or between the electrodes. Optionally, tissue and/or probe temperature sensors may also be provided.

Typically, the probe body adjacent the electrodes will comprise a thermally conductive material to enhance heat conduction from the engaged tissue surface for pre-cooling of the tissue (and for cooling the tissue engaging and adjacent the electrodes during RF heating). The body may comprise any of a variety of alternative metals such as aluminum or the like, and may comprise a thermal insulation material on the back and side surfaces. Inserts 87 will ideally comprise thermally conductive and electrically insulating structures. Inserts 87 may optionally comprise a polymer such as Derlin® or the like. In some embodiments, the thickness of inserts 87 will be minimized to enhance thermal conduction while still maintaining sufficient electrical insulation. For such embodiments, inserts 87 may comprise films of a polymer such as Mylar® or the like, or may be formed in part from anodized aluminum. Electrodes 86A will typically comprise a thermally conductive and electrically conductive metal.

In the embodiment illustrated in 12A–C, the probe has an overall length of about 3" and a width of about 2". Electrodes 86A have a length of just under an inch, a width in the range of ⅛" to ¼" and are separated by a distance in a range from about 0.2" to about ½".

Referring to FIGS. 12D and E, another cooled bi-polar probe 84B includes a pair of heating electrodes 86B mounted to a cooled probe body. Bi-polar probe 84B also includes a tissue pre-heater in the form of pre-heat electrodes 91. As can be understood with reference to FIG. 12E, as the cooled probe body draws heat from the engaged tissue surface, conduction of a pre-heating radio frequency current between pre-heat electrodes 91 in a bi-polar manner can enhance the temperature differential between the target tissue and the intermediate tissue. This allows a probe structure engaging a single tissue surface to approximate the tissue temperature profile which is desired at the time heating is initiated (as described above regarding FIGS. 3). Additionally, this enhanced temperature differential may lower the impedance of the target tissue so as to increase the current density in that region. As the cooled intermediate tissue should have a higher impedance, and as current will generally seek the path of least impedance, the pre-warmed target tissue can be heated with less collateral damage to the adjacent tissues. Note that in some embodiments, pre-heating might be used without pre-cooling to provide at least a portion of this desired temperature differential. Regardless, the temperature differential urges the current from the adjacent tissue and into the target tissue. It should be noted that a careful monitoring of adjacent tissue and/or surface impedance can be beneficial. If the impedance of the cooled tissue is raised too much, the current may travel along the surface of the probe, rather than penetrating to the target tissue. The surface impedance can be monitored and/or controlled using the surface temperature.

This generation of a preferred current path by imposing a temperature differential on the tissue prior to RF heating may be used with pre-coolers, pre-heaters, and heating electrodes having a wide variety of differing geometries. In general, pre-heating can reduce an impedance of the target tissue sufficiently to locally enhance current density such that the eventual heating of the target tissue is significantly increased. As heating progresses, the temperature differential and difference in impedance may increase, further reinforcing the selective heating of the target tissue with a positive feedback type response. The pre-heating will often be controlled so as to align the temperature differential between the target tissue and the adjacent tissue.

Similarly, pre-cooling might be used with pre-heating or without pre-heating so as to generate the desired temperature differential. Pre-cooling should enhance an impedance of a tissue sufficiently to locally reduce current density within that tissue so that its heating is significantly diminished. Pre-cooling will often be controlled to align the temperature differential between the target tissue and the adjacent tissue.

In general, localized RF heating will often make use of electrical currents which are sufficiently parallel to a boundary region between the target tissue and the intermediate tissue so that the differential impedance urges current in the desired direction.

It should be understood that pre-heating might be provided by a wide variety of energy transmitting elements, including the energy transmitting elements described herein for selective shrinkage of tissues. As can be understood with reference to FIG. 1, establishing the desired temperature differential can be aided using one or more temperature sensors coupled to the system processor. Such temperature sensors might sense the temperature of the adjacent tissue at the probe/tissue interface or within the adjacent tissue, or may alternatively sense the temperature of the target tissue using surface or needle mounted thermal couples, thermistors, diodes, or the like. Such temperature sensors will typically transmit signals of the measured target tissue temperatures to the processor, which will use these signals to determine whether the desired temperature differential has been provided. The processor may optionally vary electrical pre-heat current, a pre-heat duty cycle, a total pre-heat time, a total pre-cooling time, a probe surface temperature, a pre-cooling duty cycle, or the like.

Probe body 84B will have a total length (and an electrode length) of about 3", and will have a width of about 5". The probe body will again ideally comprise aluminum or some other body thermally conductive material. Some form of electrical insulation will often be provided between electrodes 86B, 91 and an electrically conductive probe body, as described above. The electrodes may comprise stainless steel, aluminum, or a wide variety of alternative conductive materials.

Probe 84B may also be used in an alternative mode to selectively contract the target tissues. Pre-heat electrodes 91 have larger tissue engaging surfaces than the heating electrodes 86B, and will distribute the current over a larger tissue volume. To selectively heat tissues above and/or between the heating electrodes, current may be driven between the large right electrode 91 and the small left heating electrode 84B, and then between the large left electrode and the small right heating electrode. These overlapping currents may be driven in cycles, and should help avoid over-heating and unnecessary injury to the adjacent and target tissues. A transvaginal probe 84B' including preheat electrodes 91 and an alternating, interleaved electrode control arrangement is illustrated in FIG. 12Di. Preheat electrodes EA and ED provide an initial preheat zone PH, as schematically shown in FIG. 12Dii. Current is then alternated between interleaved electrode pairs EA, EC and EB, ED (as shown) to selectively heat overlapping target zones 32A, 32B. The desired pre-determined treatment temperature is achieved in a target tissue region 32C which is separated form the electrode surfaces. A computer processor will generally control this heating process, as generally described above.

FIGS. 12F and G illustrate a still further alternative bi-polar probe structure 84C which will produce a heating pattern that is appropriate for tumors and other relatively thick localized target tissues 32'. Once again, target tissues 32' are separated from a tissue surface by an adjacent tissue AT. Probe 84C includes concentric bi-polar electrodes 86C, shown here with one of the electrodes having a circular shape and the other having an annular shape. As described above, the adjacent tissue will often be pre-cooled through the electrodes and/or the probe surface adjacent (and often between) the electrodes.

FIGS. 12H–L illustrate a cooled bi-polar transvaginal probe with temperature sensing capabilities, and a method for its use to selectively heat and contract in a pelvic fascia. Probe 84D include two needle mounted temperature sensors 95 extending from between electrodes 86D. The needle mounted temperature sensors are protected by a retractable guard 97 which is withdrawn proximately after probe 84D is inserted to the treatment location. The temperature sensors are then advanced into the tissue by moving the probe laterally as shown in FIG. 12K.

Probe 84D includes a cooling channel system 89 that cools the electrodes and the probe surface there between. The bladder wall B will preferably be cooled by circulating a chilled fluid within the bladder (as described above in FIG. 6), and pre-cooling of vaginal wall VW will often be computer controlled using feedback from the temperature sensors. Optionally, computer control based on this feedback might also (or instead) be provided to control pre-heating where pre-heating capabilities are included in the probe. Temperature sensors 95 might be used to measures the temperature at the probe/interface, within the vaginal wall, within the endopelvic fascia, or the like. Regardless, pre-chilling of probe 84D and within bladder B will often be timed and controlled so as to provide a temperature profile similar to that illustrated in FIG. 3B upon the initiation of the heating current between electrodes 86D.

Theoretically, if heating were initiated while the bladder wall, endopelvic fascia, and vaginal wall were at a uniform temperature, the current density produced by electrodes 86D would result in considerable collateral damage when heating the endopelvic fascia to the desired contraction temperature range. This uniform temperature current density is schematically illustrated by dashed lines 99. However, as the bladder wall and the vaginal wall have been cooled to enhance their impedance, the electrical current will tend to move the current into to the warm endopelvic fascia EF, thereby enhancing localized heating of this target structure. This tailored current density is schematically illustrated by solid lines 101 in FIG. 12L. This tailored current density effects the desired contraction of the target endopelvic fascia while minimizing damage to both adjacent tissues.

Figure 13:
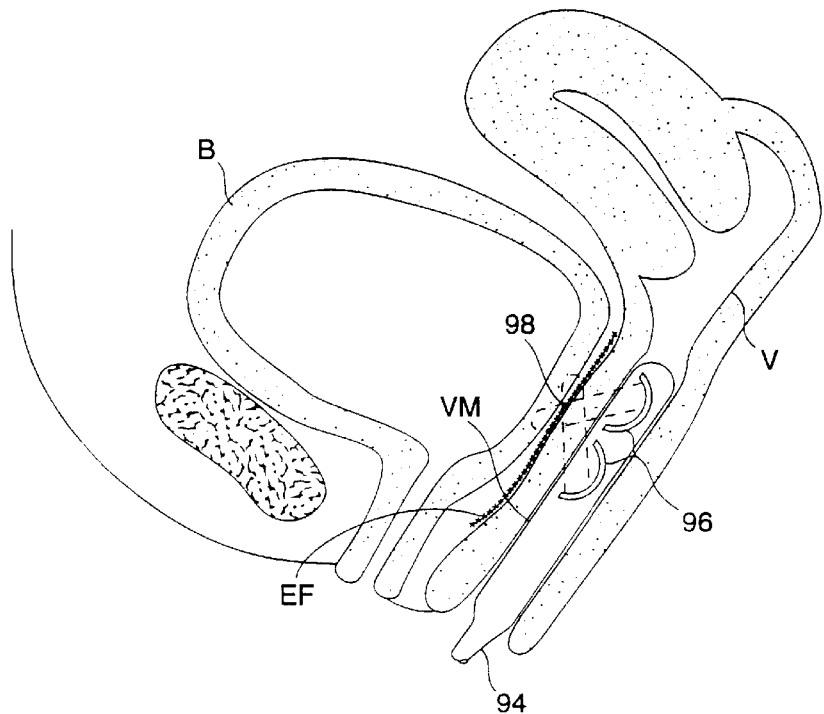
FIG. 13 schematically illustrates a method for selectively shrinking endopelvic fascia by transmitting microwave or ultrasound energy from a cooled vaginal probe.

Referring now to FIG. 13, microwave probe 94 includes microwave antennas 96 which direct microwave heating energy 98 through the vaginal wall VW and onto endopelvic fascia EF. Microwave probe 94 will again typically include a cooled probe surface to minimize damage to vaginal wall VW. The microwave may optionally be produced by a phased array microwave antenna to decrease heating next to the cold probe relative to the heating of endopelvic fascia EF, or a more conventional microwave antenna may be used.

Microwave power having a frequency of about 2250 MHz is most often used for heating. However, the use of extremely high frequency microwaves would permit constructive interference at the intersection of microwave energy streams by control of the microwave frequency, phase, and electrode spacing. Such constructive interference of microwaves may be used to enhance the heating of the target tissue relative to the heat produced in the intermediate tissue between microwave probe 94 and endopelvic fascia EF (in this example). Injection of an electrically insulating fluid, such as Dextran™, may be used to absorb microwave energy and protect tissues beyond the target zone. In some embodiments, injection of a liquid contrast medium might be used to enhance visualization of the treatment region, increasing the visibility and clarity of the vagina V, bladder B, the other adjacent organs, and the spaces therebetween. Such a contrast medium will typically be highly visible under ultrasonic or fluoroscopic imaging modalities.

An alternative form of energy which may be used in a probe schematically similar to that illustrated in FIG. 13 is ultrasonic heating. A cooled ultrasonic probe could be used to provide heating of the endopelvic fascia adjacent the vagina, preferably while protecting the adjacent tissues using a material which reflects ultrasound. Suitable protection materials include $CO_2$ or a liquid/foam emulsion material. High intensity ultrasound is able to heat tissues at a distance from the probe, and may be focused to apply the most intense heating at a particular treatment site. Concentration of ultrasound energy deep in the body may avoid heating of tissues at the entry site of the focused ultrasound beam, although gas pockets and bony structures may absorb and/or reflect the focused ultrasound energy, so that tissues may be damaged by both localized heating and cavitation. Once again, the surface of an ultrasound probe will typically be cooled to protect the tissues which are directly engaged by the probe.

The absorption of ultrasound energy is generally proportional to its frequency. A frequency on the order of about 10

MHz would be appropriate for penetration a distance on the order of about 1.0 cm into tissue. The focal accuracy is dependent on the wavelength, and at about 10 MHz the wavelength is about 0.15 mm. As a result, a very sharp focus is possible. Although the absorption coefficient will vary with the tissue type, this variation is relatively small. Hence, it is expected that the focusing of an ultrasound beam will have a greater influence on power dissipation in the intermediate tissue than will the variation in absorption coefficient due to differing tissue types.

Figure 13A:
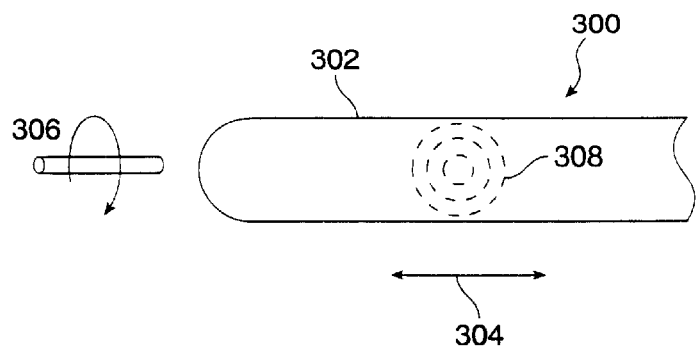
FIGS. 13A–M illustrate alternative focused ultrasound probes for remotely heating tissues, the probes having phased array ultrasound transmitters with either an annular or linear array geometry.

As illustrated schematically in FIG. 13A, a focused ultrasound probe 300 having an elongate probe housing 302 is well adapted to accommodate axial translation 304 and rotation 306 of an ultrasound transducer 308. To treat arbitrary structures by selectively varying the focal depth of transducer 308, the transducer can optionally be in the form of an annular array.

It may be possible to make use of a fixed focal length transducer. Such a fixed transducer will preferably be adapted to focus at a depth appropriate for the desired therapy. In some embodiments, it may be possible to translate such a fixed focal length transducer relative to the fascial layer to treat tissues at differing depths. Alternatively, by making use of the multiple elements of a phased array, the transducer can be dynamically focused on the treatment region by phasing the excitation drive current to the array elements. Advantageously, treatment may be performed using a continuous wave excitation, significantly facilitating phasing of the drive currents to the individual array elements.

Figure 13B:
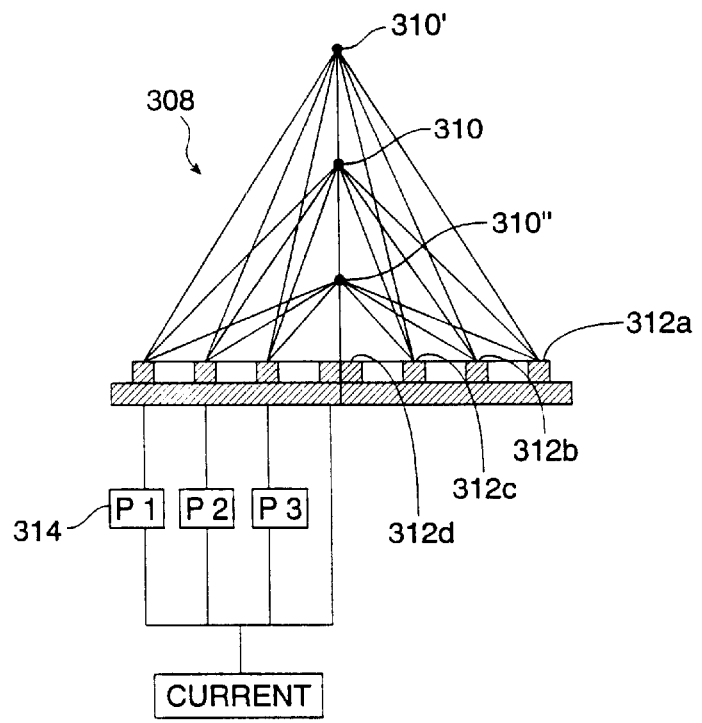
Figure 13C:
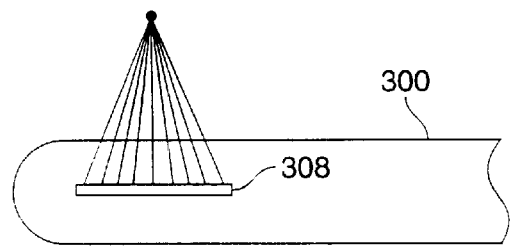

As illustrated in FIGS. 13B and C, annular arrays are particularly well adapted for focusing ultrasound energy at a focus point 310. By varying the electrical current supplied to the individual annular shaped elements 312a, 312b, . . . of annular array 308 using phase control 314, the focal depth of the annular array can be increased to 310' or decreased to 310".

While the ultrasound emitting structure is herein generally referred to as a transducer, ultrasound transmitters which do not also sense ultrasound energy might be used. Nonetheless, it may be advantageous to both image and heat the tissue using a single transducer structure. The transducer may be excited with an impulse, or with a continuous signal where a longer duty cycle is desired. By alternating imaging and heating, the changes in the thickness or ultrasonic appearance of the tissue may be monitored to determine when the tissue has completed its treatment.

The ability to measure the thickness of fascia and other collagenated tissues using ultrasound energy is particularly advantageous for judging the completeness and/or efficacy of the thermal shrinking treatment. Hence, heating may be controlled and terminated based on ultrasound feedback regarding the thickness and/or change in thickness of fascia or other collagenated tissues. The generation of harmonics or subharmonics of the fundamental carrier frequency is an indication of the production of cavitation in the tissue, and may be used as a feedback mechanism for adjusting ultrasound power or scanning speed. Ultrasound sensed target tissue thickness feedback and control may be incorporated into probes which heat the target tissue using ultrasound, RF energy, microwave, or any other energy transmitting mechanism, within the scope of the present invention.

To make use of ultrasound's thickness sensing capabilities, an initial target tissue thickness may be measured and stored. During the course of treatment, the thickness of the fascial layer (or other target tissue) can be remeasured, and the revised tissue depth may be compared to the initial tissue depth. Changes in a fascial layer tissue depth during treatment may then be used as a guide to the progress and completion of the tissue shrinkage operation. Depth determination may be made using an external imager, or might be provided by an imaging A-scan from the treatment transducer.

In some embodiments, computer feedback may be used to guide the user in the application of ultrasound energy using ultrasound probe 300. For example, a computer controller may display the location of fixed reference points (such as bony structures) together with a representation of the physical location of the probe. Such a display would help illustrate the location relative to the bony structures, which may help the user dynamically guide the probe to the desired treatment area. In some embodiments, such a relative location image may be provided using an external ultrasonic imager. In such embodiments, the bony structures, the treatment probe, any temperature sensing needles, and the fascia or other target tissues could all be visible within a single image. This would greatly facilitate guiding of the probe, and may be used to selectively activate the probe so as to treat the target tissues, either manually by the user or automatically under computer control.

Figure 13D:
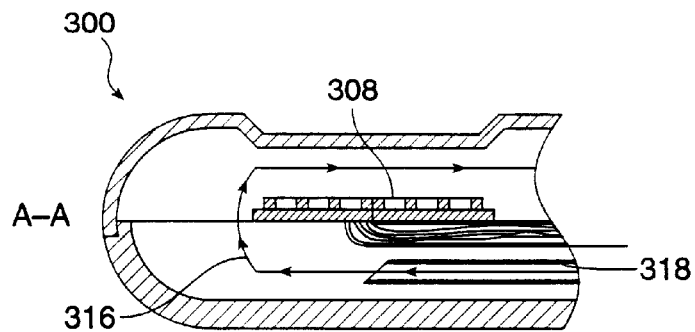
Figure 13E:
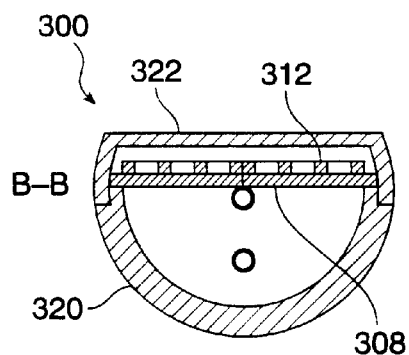
Figure 13F:
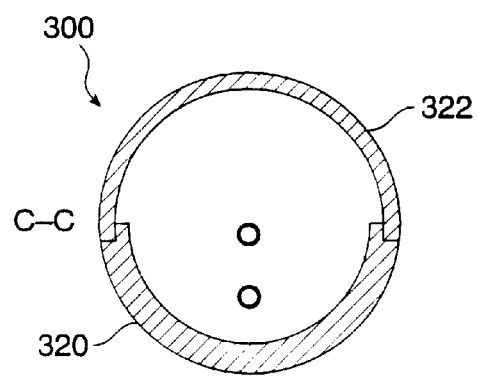
Figure 13G:
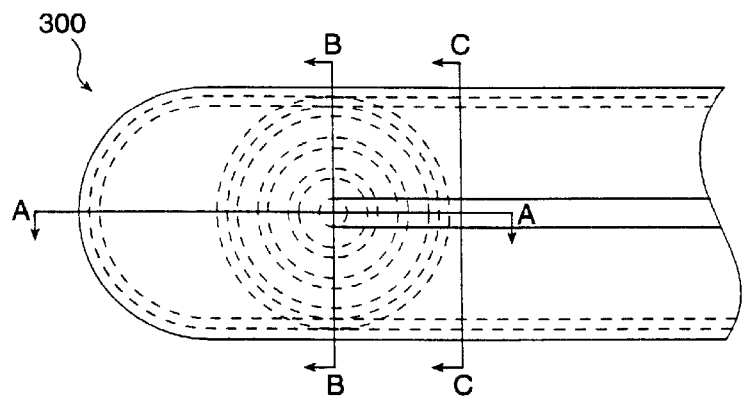

The structure of ultrasound transducer 300 is illustrated in more detail in FIGS. 13D–G. As illustrated in FIG. 13D, coolant flow 316 will preferably be provided through a cooling lumen 318, with the cooling lumen distributing a cooling fluid adjacent annular transducer 308. In addition to the chilling of tissues provided by cooling flow 316 (which can protect intermediate tissues outside the treatment zone), it is highly beneficial to cool the transducer itself, as transducers typically have an efficiency of about 60% or less. For a delivered power of about 100 W, the input power would typically be about 167 W. As a result, 67 W of heat should be removed from the housing adjacent the transducer so as to prevent the surface of the transducer housing from rising above about 45° C. As described above, it will often be desirable to chill the intermediate tissue engaged by the probes of the present invention to temperatures significantly lower than this. It should at least be possible to maintain the housing below a maximum safe tissue temperature by using an adequate flow a cooling liquid such as water, and still further cooling may be possible.

It will also be desirable to provide liquid surrounding the probe to acoustically couple the housing of the ultrasonic probe to the intermediate tissue. For example, providing a physiologically benign liquid, such as isotonic saline or Dextran™, between an ultrasonic vaginal probe and the vaginal wall will facilitate the transmission of ultrasonic power from transducer 308, through the cooling fluid and housing of the transducer, and into the vaginal wall. In some embodiments, the liquid between the probe and the intermediate tissue may also contain a bioactive and/or therapeutic agent, such as an anti-biotic drug to further lessen the chances of infection after the procedure.

In the exemplary embodiment illustrated in FIGS. 13D–G, the housing of the probe is defined by a thick lower wall 320 and a thin upper wall 322. The use of a thinner upper wall, which will generally be disposed between transducer 308 and the target tissue, will enhance the efficiency of acoustic coupling between the transducer and the target tissue.

An alternative ultrasound probe 330 having a linear array transducer 332 is illustrated in FIGS. 13H–M. This embodiment includes many of the features and advantages described above with reference to ultrasound transducer 300, but linear array transducer 332 includes a plurality of linear array elements 312a, 312b, . . . .

In general, ultrasonic probes having a fixed, radially symmetrical transducer can be focused to a point having a size on the order of 1 wavelength. Ultrasonic probes having transducers with cylindrically symmetrical designs will generally focus to a line with a theoretical thickness on the order of 1 wavelength, and with a length similar to the length of the cylindrical transducer.

In the case of a fixed radially symmetrical transducer, the probe will preferably have an internal structure which permits the transducer to rotate about the axis of probe, and also to translate along this axis. In the case of a fixed cylindrically symmetrical transducer, the internal structure of the probe will preferably allow the transducer to rotate about the axis of the probe, and may also be used to dither the rotational position of the transducer about a nominal orientation. It may also be preferable to include at least some axial translation or scanning capabilities for fixed cylindrically symmetrical transducers.

If the transducer has a fixed focal length, it is generally advantageous to provide the transducer assembly with the ability to translate radially with respect to the axis of the probe, so that the fixed focus of the beam can be positioned at the correct depth within the tissue to be treated. The complexity of this radial translation capability is obviated by providing linear array transducer structures having dynamic depth focusing capabilities.

Figure 13H:
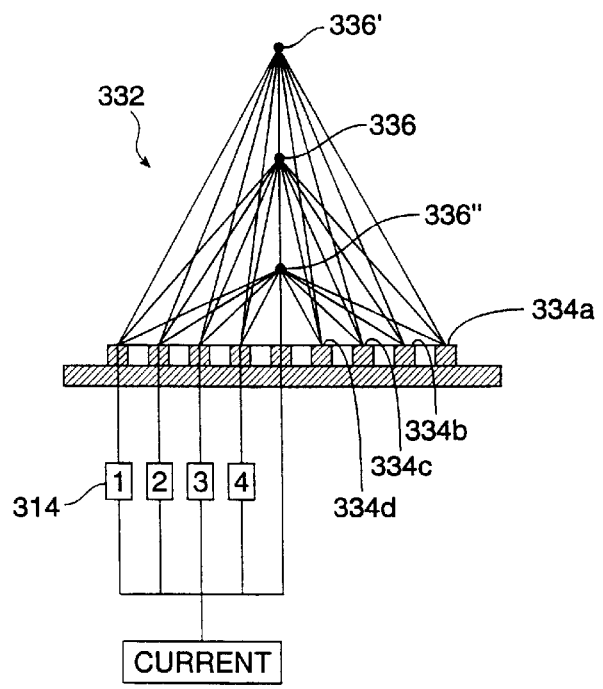
Figure 13I:
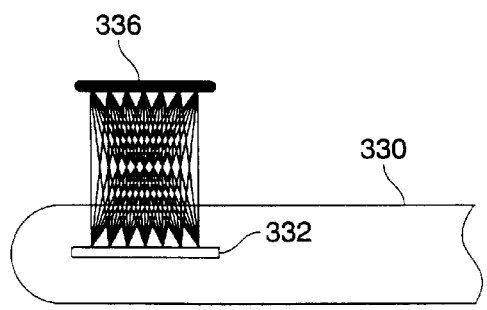
Figure 13J:
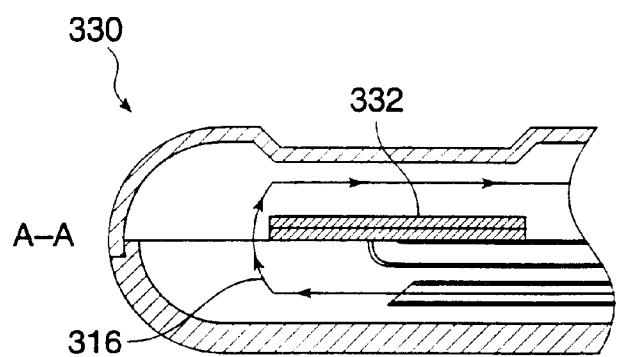
Figure 13K:
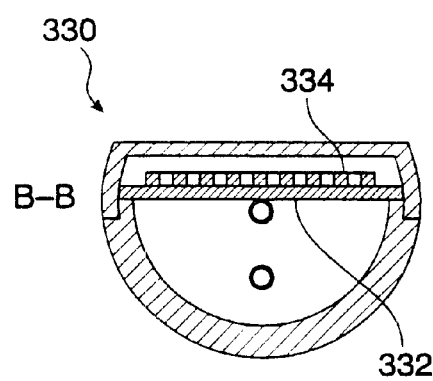
Figure 13L:
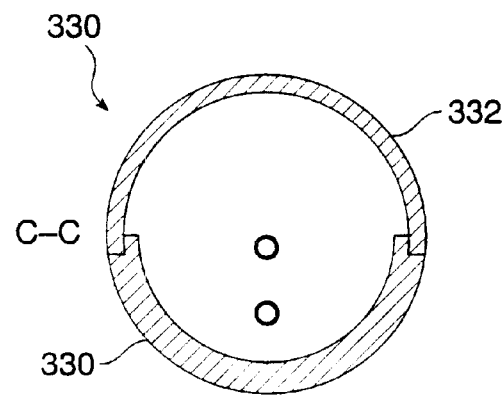
Figure 13M:
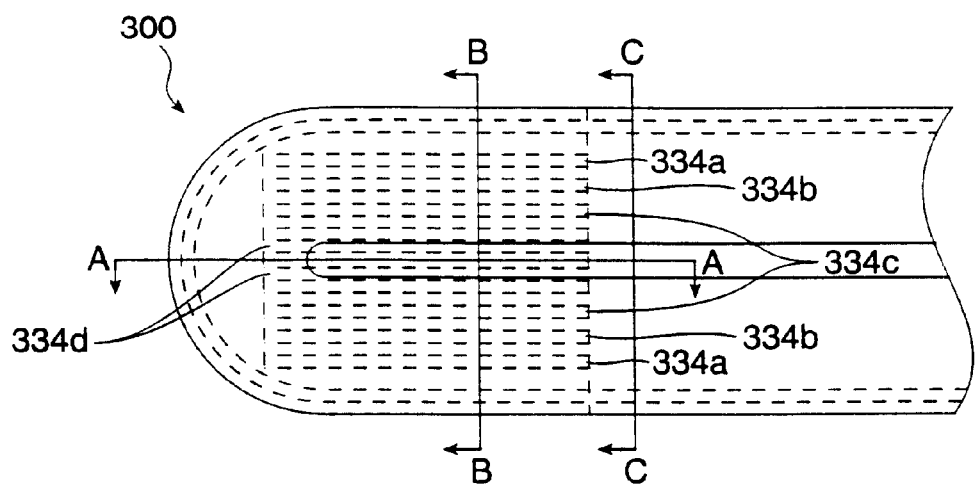

As illustrated in FIG. 13I, linear array transducer 332 will also generally focus the ultrasound energy on a line 336. Advantageously, the focal distance between the transducer and line 336 can be varied using phase control 314. In other words, changing the phase of the individual linear transducer elements allows the radial position of the focal line to be varied, from line 336' to line 336" as illustrated in FIG. 13H. Where linear elements 334 are oriented parallel to the axis of the probe, such a linear array is particularly well suited for treating tissue layers that are roughly parallel to the probe.

In general, a controller will coordinate the transducer drive current with the location, angle, and focusing depth of the transducer, so that the transducer is driven only while positioned such that the focus of the ultrasonic beam is within the target tissue. The controller and the associated positioning mechanism will generally keep the array oriented toward and focused on the target tissue throughout much or all of the scan so that the transducer can be providing heat energy most of the time.

Should it be desirable to combine a commercial ultrasonic imaging vaginal probe with an ultrasonic power treatment device, it will generally be preferable to position the two transducers adjacent to each other on a single internal transducer scanning assembly. This can facilitate rotating and translating the imaging and therapeutic ultrasonic transducers together, so that the structure to be treated is alternately viewed and heated. Ideally, these alternate viewing/therapy cycles will be coordinated so that one or the other is being performed substantially continually.

In some embodiments, it may be beneficial to update the target location of the fascia or other target tissue throughout the procedure. This will allow the therapy to remain focused upon a support tissue such as the endopelvic fascia, even when the support tissue is changing in shape and/or position, which will often occur during a successful treatment.

Figure 14:
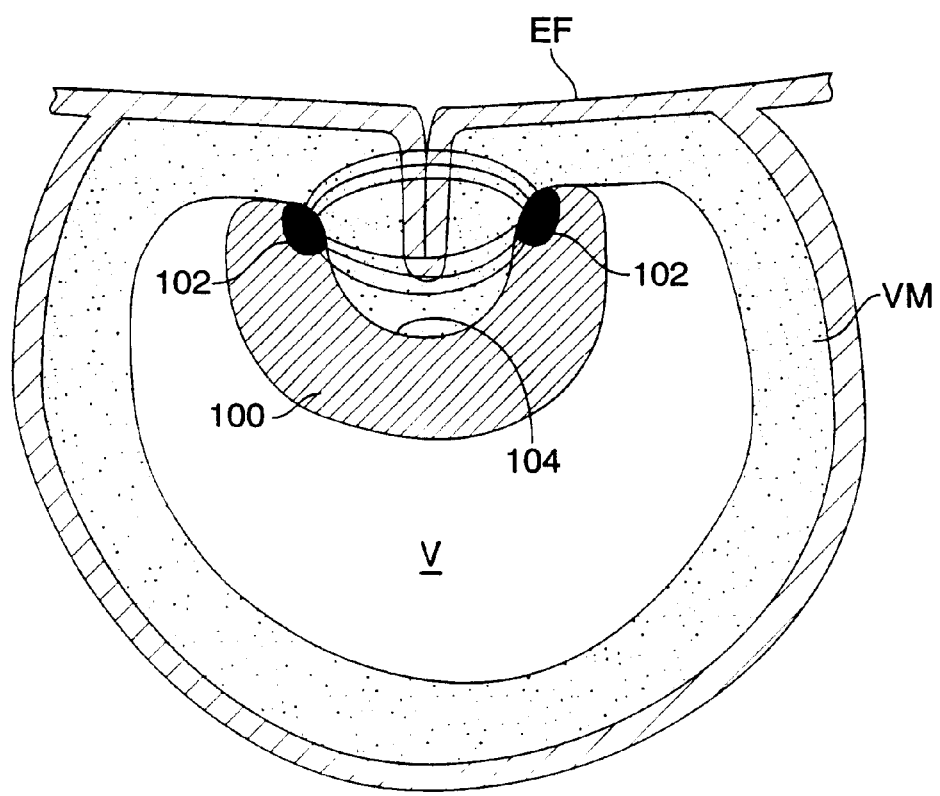
FIG. 14 is a cross-sectional view illustrating a method for selectively shrinking endopelvic fascia by grasping and folding the wall of the vagina or colon to facilitate focusing of heating upon the fascia, and to enhance shrinkage of the fascia by decreasing tension in the fascia while the fascia is heated, according to the principles of the present invention.
Figure 15:
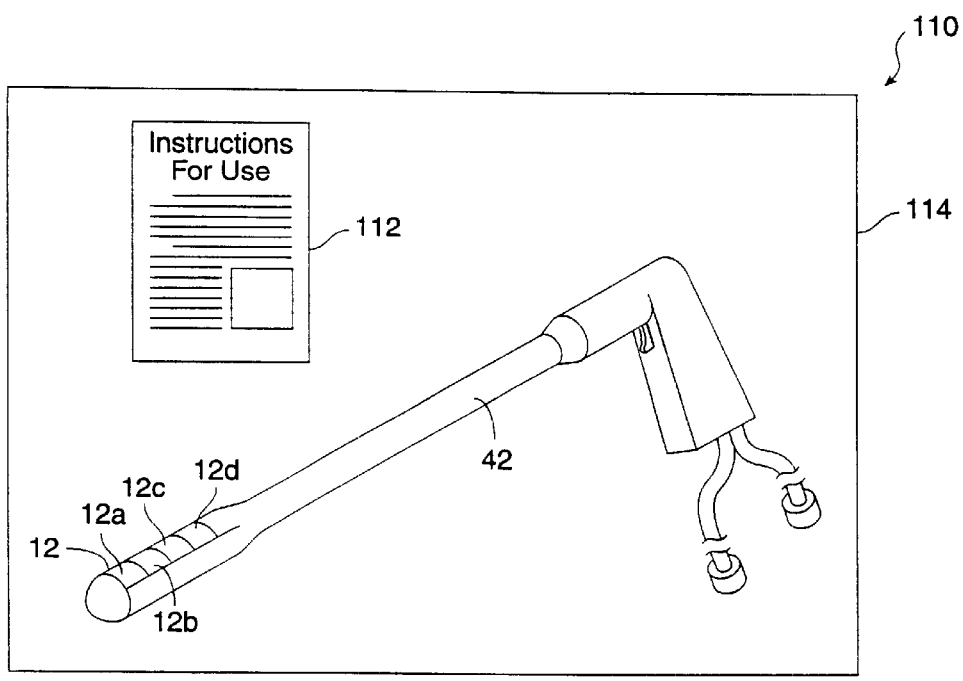
FIG. 15 is a schematic illustration of a kit including the vaginal probe of FIG. 5, together with instructions for its use to shrink tissues, according to the methods of the present invention.

A cross-section of a grasping bipolar probe 100 is illustrated in FIG. 14. Grasping probe 100 grips and folds an anterior portion of the vaginal wall, together with the endopelvic fascia EF, as shown. It should be understood that the targeted fascia may be separated from the probe by muscle, vasculature, and the like, as well as by vaginal wall VW. Endopelvic fascia EF is typically about 1 mm thick, while the grasped, folded vaginal wall will typically be between about 10 mm to 14 mm thick. The folded endopelvic fascia EF may thus be heated and contracted between cooled bipolar electrodes 102, as described above. Depending on the length of the fold, cooled bipolar electrodes 102 may optionally be formed as wide elongate plates. Grasping may be accomplished mechanically or by applying a vacuum to draw the vaginal wall into a cavity 104 of grasping probe 100. By drawing the endopelvic fascia into close proximity of both electrodes, a finer focusing of the heating may be accomplished, thereby minimizing the damage to adjacent tissues. Additionally, grasping probe 100 may draw the tissue inward to relieve any tension in the fascia, thereby enhancing the shrinkage. As described above regarding FIG. 12, $CO_2$ or some other insulating medium may be used for additional protection of adjacent tissues and organs.

A kit 110 includes vaginal probe 42 and instructions 112 for use of the probe to shrink tissues, the probe and instructions disposed in packaging 114. The instructions may set forth the method steps for using probe 42 described hereinabove for selectively shrinking pelvic support tissues as a therapy for urinary incontinence, or may alternatively recite any of the other described methods. Additional elements for system 10 (see FIG. 1) may also be included in kit 110, or may be packaged separately.

Instructions 112 will often comprise printed material, and may be found in whole or in part on packaging 114. Alternatively, instructions 112 may be in the form of a recording disk or other computer-readable data, a video tape, a sound recording, or the like.

Figure 16A:
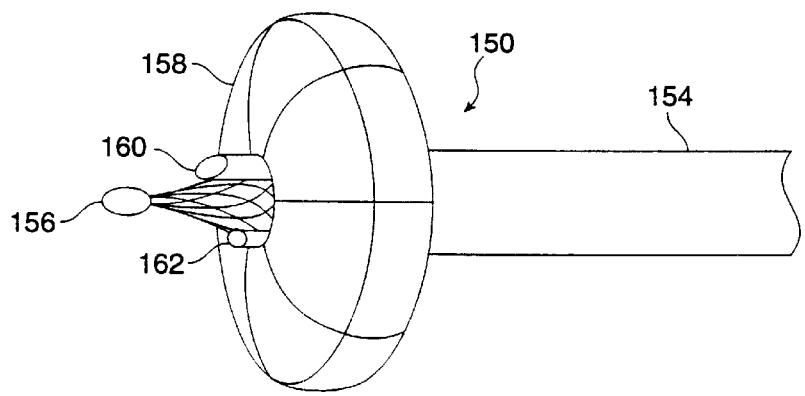
FIGS. 16A–C illustrate structures and methods for selectively transmitting an RF current flux through a conductive fluid within the bladder while cooling the bladder wall with the fluid, according to the principles of the present invention.
Figure 16B:
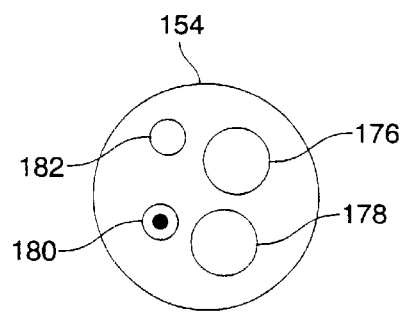
Figure 16C:
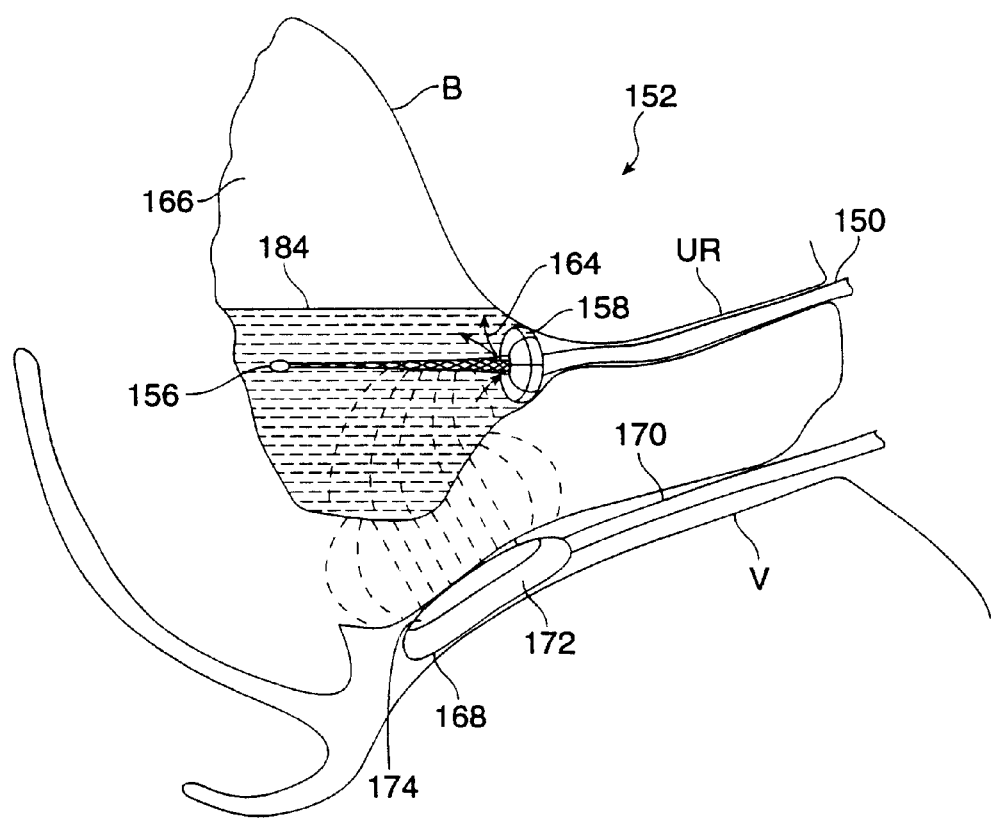

Referring now to FIGS. 16A–C, a transurethral probe 150 may be used to shrink endopelvic fascia between bladder B and vagina V using a conductive fluid electrotherapy system 152. Transurethral probe 150 includes a shaft 154 having an electrode 156 near its distal end. A toroidal balloon 158 seals around the shaft to prevent fluid communication between bladder B and urethra UR. Fluid in-flow and out-flow ports 160, 162 allow both gas and liquid to be introduced into the bladder in controlled amounts, and also allow a conductive fluid 164 (typically an electrolytic liquid, and ideally comprising a chilled saline solution), to be circulated within the bladder.

An insulating fluid 166 having a density much less than that of conductive fluid 164 occupies a portion of bladder B away from the tissues targeted for treatment. As electrode 156 is within conductive fluid 164, the conductive fluid can transmit RF current between the electrode and a cooled plate electrode of a vaginal probe 168. The conductive properties of conductive fluid 164 may be optimized for both conduction of electricity (for example, by controlling the salinity of a saline solution), and for directly transferring heat from the bladder wall.

A cross-section of shaft 154 is illustrated in FIG. 16B. As described above, an in-flow lumen 176 allows the introduction of both insulating fluid 166 and conductive fluid 164 through in-flow port 160. An out-flow lumen 178 is similarly in fluid communication with out-flow port 162 to allow recirculation of chilled saline or the like, and also to facilitate removal of the fluids from the bladder after the procedure. RF energy is provided to electrode 156 through wire 180, and a balloon inflation lumen 182 allows transurethral probe to be inserted and removed with a minimum amount of trauma, while still ensuring an adequate seal of the body cavity. Electrode 156 may extend within the bladder (as shown in FIG. 16C) to increase the electrode surface area exposed to conductive fluid 164. This may help minimize localized heating at the electrode surface. Inadvertent contact between the bladder wall and electrode surface may be avoided by surrounding the electrode surface with a protective mesh.

In the embodiment of FIG. 16C, vaginal probe 168 includes a flexible shaft 170 and a distal balloon 172. Engagement between an electrode 174 and the vaginal wall is enhanced by inflating the balloon within vagina V, while cooling of the electrode surface may be provided by circulating fluid within the balloon. The electrode may have a flat electrode surface with rounded edges, as described above.

In use, the patient will be positioned on her back (so that the portion of the endopelvic fascia targeted for shrinkage is disposed vertically below the bladder), and transurethral probe 150 will be introduced through urethra UR to bladder B. Toroidal balloon 158 can then be inflated to seal around the transurethral probe, and the bladder can be partially filled with insulating fluid 166, typically using air or a gas such as carbon dioxide. The bladder is also partially filled with conductive fluid 164, typically in the form of a chilled electrolytic liquid such as saline. The bladder wall may be further cooled by cycling the chilled saline before, during, and/or after heating, as generally described above regarding FIGS. 2 and 3.

The volumes of the fluids introduced into the bladder will be selected to provide therapy over the target tissue, and to minimize heating beyond the target tissue. Preferably, the volumes and positions of conductive fluid 164 and insulating fluid 166 are maintained throughout the procedure. As electrode 156 is in contact with conductive fluid 164, the conductive fluid effectively forms a large area electrode at the floor of the bladder, while the gas provides an electrical (and thermal) insulator at the top of the bladder. Maintaining the relative volumes of fluid limits heating to below a gas/liquid interface 184.

Transvaginal probe 168 is introduced and positioned to the extreme right or left side of the pelvis so that electrode 174 is oriented towards the interface between conductive fluid 164 and the lower right side or lower left side of the bladder wall. Probe balloon 172 can then be inflated, and the bladder wall and vaginal mucosa can be pre-chilled by circulating fluid through the probes. Once these tissues are properly pre-cooled, heating can proceed as described above, with the conductive fluid/bladder wall interface acting as one plate electrode, and electrode 174 on balloon 172 of vaginal probe 168 acting as the other. As was also described above, the electrode of vaginal probe 168 may be segmented to target heating on the target tissue, and to minimize any unwanted concentrations of heating caused by the variations in total tissue depth, non-parallel tissue surface effects, and the like.

Figure 17A:
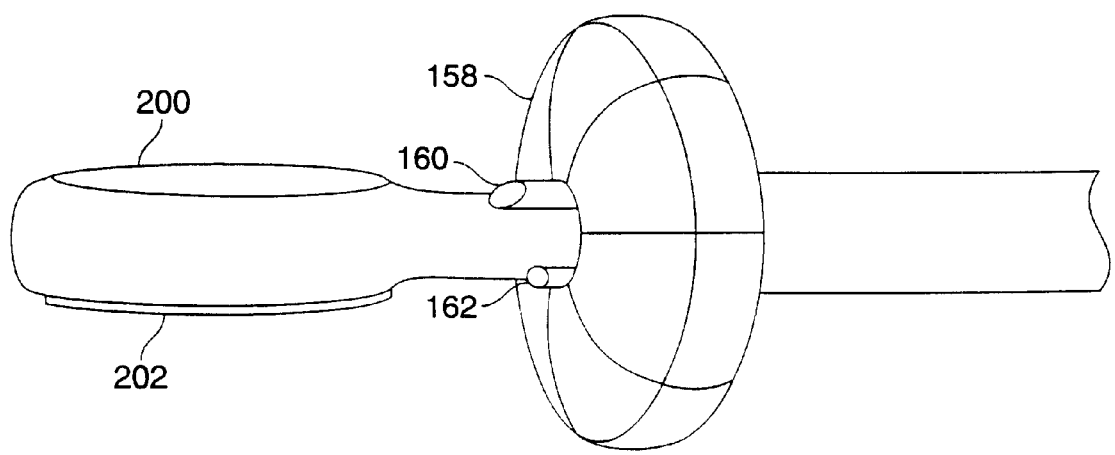
FIGS. 17A and B illustrate an alternative probe for use with a conductive fluid, the probe having both a toroidal balloon for sealing the conductive fluid and an insulating gas within the bladder, and a spoon shaped balloon supporting an electrode surface, whereby the endopelvic fascia between the bladder electrode and a cooled plate electrode of a vaginal probe may be heated and shrunk.
Figure 17B:
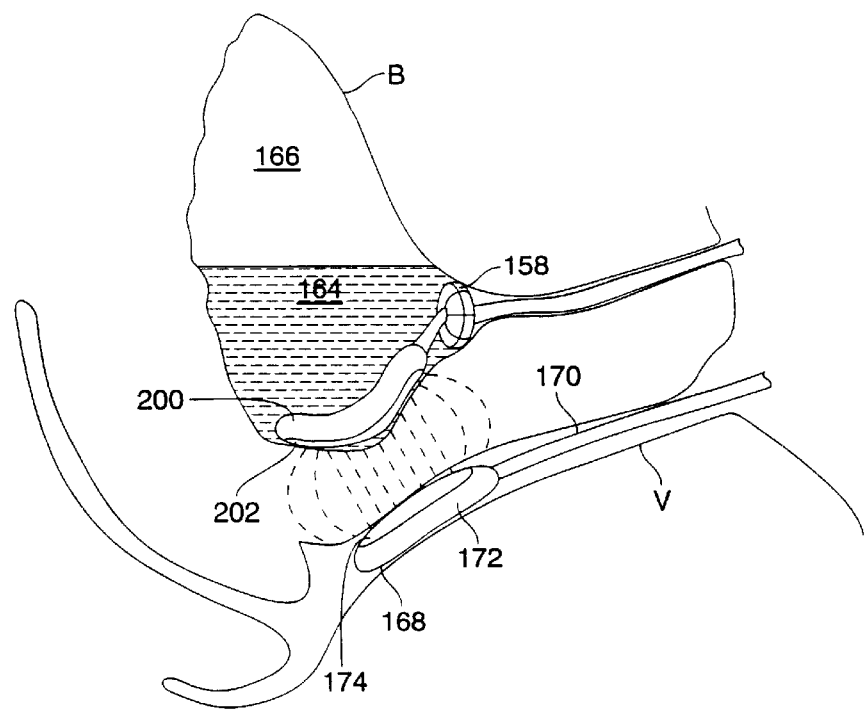

Referring now to FIGS. 17A and B, a similar method for shrinking endopelvic fascia to that described above regarding FIGS. 16A–C may be practiced using a transurethral probe having an inflatable spoon shaped balloon 200. Spoon shaped balloon 200 supports a deployable electrode 202, and can be used to orient the deployable electrode toward vaginal probe 168. This may enhance control over the heating current flux, and spoon shaped balloon 200 (as well as balloon 172 of vaginal probe 168) may be insulated away from the electrode surface to further limit injury to the bladder wall. Deployable electrode 202 may also be segmented as described above, and will provide a small cross-sectional profile prior to inflation so as to minimize trauma during insertion.

Figure 18A:
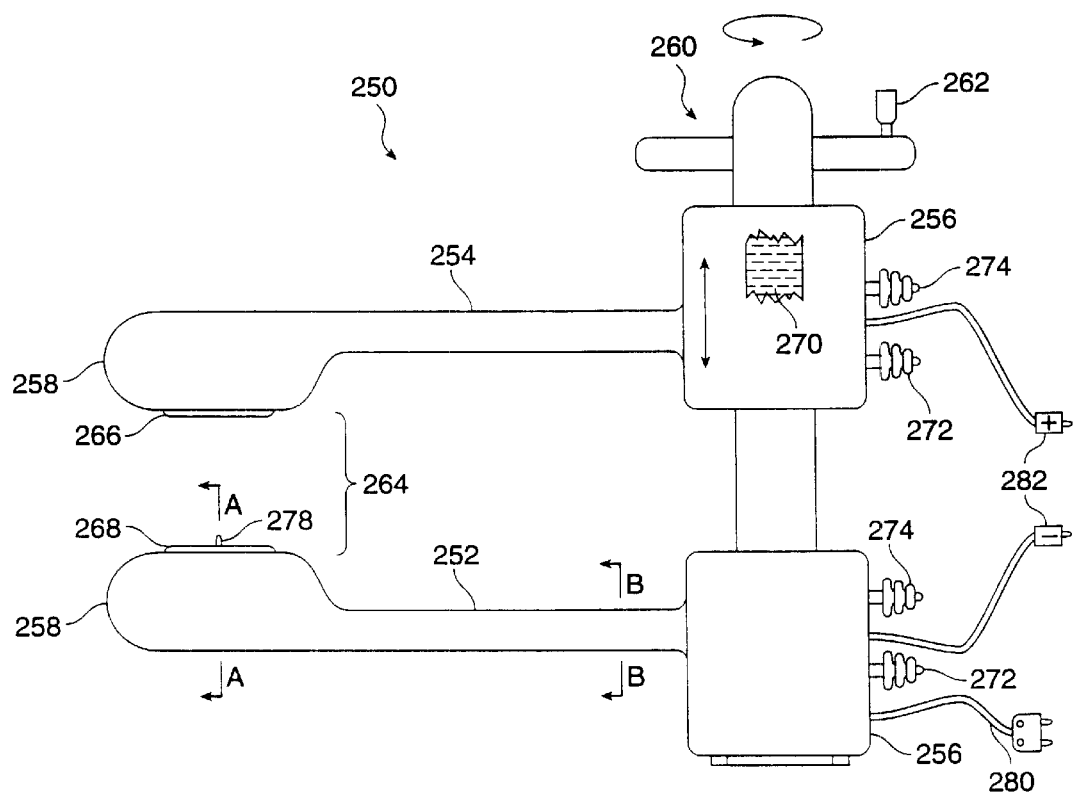
FIGS. 18A–C illustrates a clamping structure having a transvaginal probe and a transrectal probe, in which each of the probes includes an electrode surface, and in which the probes are mechanically coupled by a clamping structure for compressing the targeted endopelvic fascia (together with intermediate tissues) between a pair of opposed, cooled plate electrodes.
Figure 18B:
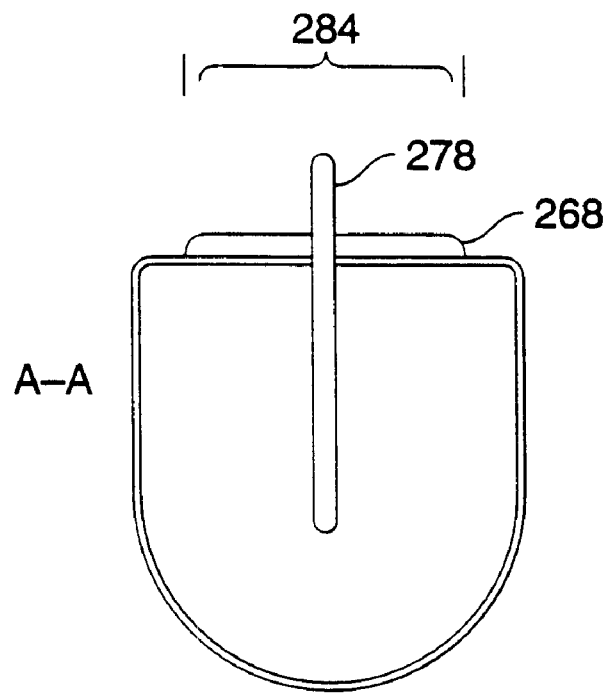
Figure 18C:
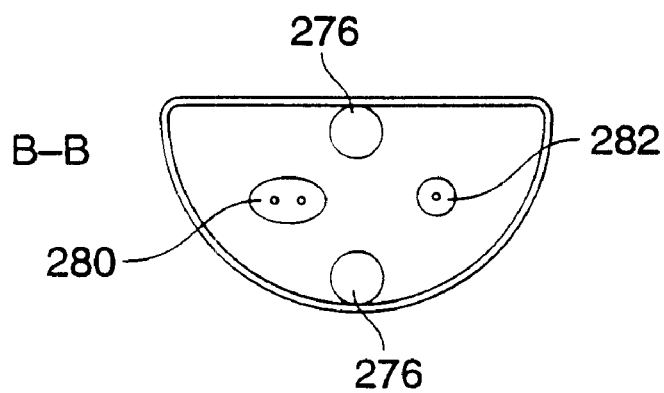

A two probe device 250 is illustrated in FIG. 18A. Two probe device 250 will be used in a method similar to that described above with reference to FIG. 6, but here includes both a transvaginal probe 252 and a transrectal probe 254. Each of these probes includes a proximal end 256 and a distal end 258. The distal ends are sized and shaped for insertion into their respective body cavities. Proximal ends 256 are mechanically coupled by a clamp structure 260. Rotating a handle 262 of clamp structure 260 changes a separation distance 264 between electrodes 266, 268 via threads 270. Hence, clamping structure 260 helps maintain the parallel alignment between the electrodes, and also helps to compress the tissue between the electrode surfaces.

It should be understood that a wide variety of mechanical actuators might be used in place of the threaded mechanism illustrated in FIG. 18A. Parallel bar linkages, ratcheted sliding joints, rack-and-pinion mechanisms, and recirculating ball linear actuators are just a few examples of alternative mechanisms which might be used. In some embodiments, the probes may be inserted independently, and then coupled together using a releasable clamping structure.

A wide variety of actuators may also be used in place of handle 262, including electromechanical actuator, pneumatic actuators, and the like. In some embodiments, the clamping structure may provide feedback on separation distance 264. More complex arrangements are also possible, in which the structure coupling the probes includes joints or flexible structures with position indicating capabilities. Such structures may provide feedback for driving segmented electrodes so as to selectively tailor the heat energy, often to evenly heat the desired target tissues by compensating for any misalignment between the electrodes, angularity between the electrode surfaces, and the like, was generally described with reference to FIGS. 2–2D.

Probes 252, 254 will also include many of the structures described above, including a cooling system having in-flow ports 272 and outflow ports 274 to cool electrodes 266, 268 through cooling system lumens 276. A needle mounted temperature sensor 278 may be advanced into the clamped tissue from adjacent one electrode to provide feedback on the heating/cooling of tissues. Such temperature information may be transmitted to a controller using temperature sensor wires 280. RF energy will be transmitted down the probes via electrode conductors 282.

In use, two probe clamp 250 will be positioned with one of the probes extending into the rectum, and the other probe extending into the vagina. Clamping structure 260 will be actuated using handle 262 to decrease the separation distance 264, and to clamp the target tissue between electrodes 266, 268. Needle mounted temperature sensor 278 will extend into the clamped tissue, ideally extending into the target tissue.

Clamping of the tissue will help ensure firm engagement between the electrodes and the tissue surfaces, and will also promote even heating by minimizing the ratio between separation distance 264 and electrode widths 284. The clamp structure is sufficiently stiff to maintain the electrode structures substantially in alignment, and also to maintain the electrode surfaces roughly parallel to each other, so as to be capable of providing sufficiently uniform current flux to shrink the target tissue. Where the electrodes are segmented (as described above), the clamping structure may accommodate significant angularity between the electrode surfaces, as well as some axial and lateral misalignment, while still effectively heating and shrinking the target tissue with minimal collateral damage. In the exemplary embodiment, electrodes 266, 268 are positioned at closer proximity to each other than probes 252, 254 proximal of the electrodes. This avoids injury to tissues proximal of the electrodes, particularly to the rectal and vaginal sphincters, when the clamping mechanism brings the probes together.

While two probe device 250 is illustrated having two separate probes which are both adapted for insertion into the body, it should be understood that a similar clamping structure may make use of a single insertable probe carrying an electrode, and a second electrode support structure adapted for use on the exposed skin. In some embodiments, it may be preferable to limit heating of the skin engaged by using an external electrode having a surface which is significantly larger than that of the internal electrode. This may reduce and/or eliminate the need for active cooling of the external electrode, and will concentrate heating closer to the smaller, cooled internal electrode surface.

The transvaginal/transrectal two probe device of FIG. 18A is particularly suitable for use as a therapy for rectocele. Similar probe structures will find use in a wide variety of applications, including many of those described above, as well as those described in U.S. patent application Ser. No. 08/910,370, filed Aug. 13, 1997, previously incorporated by reference. For example, the vaginal wall (including the endopelvic fascia) may be drawn downward between a pair of electrodes for selectively shrinking of the pelvic support tissues as a therapy for incontinence. Similar therapies may be possible for the colon.

In some embodiments, a vaginal probe similar to those described above may be mechanically coupled to a rectal probe for stabilizing the position of the vaginal probe. The rectal probe may optionally include a balloon to apply pressure to the vaginal probe, thus squeezing the two probes together. This may help to stabilize the location and direction of the vaginal probe so that it can provide heating to the deep tissues above and to the sides of the vagina. Such a stabilized vaginal probe may be used with many of the energy transmitting structures described above, including focused ultrasound transducers.

Still further alternative structures may be used to enhance positional accuracy of the probes of the present invention within body cavities such as the vagina. For example, an O ring may be sized to fittingly engage the surrounding vaginal wall so as to provide mechanical stabilization. Such an O ring may be variable in size, or may be available in a variety of selectable sizes. In some embodiments, mechanical stabilization may be provided using an inflatable cuff disposed around the shaft of the probe. Such a cuff could be inflated after the probe is positioned to engage the surrounding tissue to provide mechanical stabilization.

A fixed reference marker might also be used for positioning and/or position verification. A reference marker might be attached to the pubic symphysis, or to some other convenient bony structure. Such a marker may be used to position the probe, to measure the relative position of one or more probes, or to correct the calculated position of the probe relative to the target tissue, relative to a second electrode, or the like.

An adhesive surface or sticky pad on the probe may allow the probe to adhere to the inner vaginal surface. It may be preferable to adhesively affix only a portion of the probe, particularly where an alternate portion can translate and/or rotate with respect to the fixed portion. This might permit the treatment region to be conveniently controlled with reference to the fixed portion. A similar (and more readily releasable) result may be provided by using a vacuum attachment mechanism.

Still further mechanical mechanisms are possible. In some embodiments, it may be desirable to provide an external fixture to hold an energy applying probe with reference to bony structures of the body. Such an external fixture may provide a mechanism for translating the treatment probe along a trajectory which optimally treat the targeted fascia.

Two-probe devices may also be used in a minimally invasive, or even in a standard open procedure. For example, a pair of substantially parallel needles may be inserted on either side of a target tissue. The needles will preferably be insulated along a proximal portion and electrically and thermally conductive adjacent a distal region. RF energy may be driven between the conductive distal regions of the needles to heat the tissue therebetween. Such needle electrodes will preferably include radially expandable structures such as balloons supporting the conductive distal regions. This allows a radius of curvature of the conductive distal regions to be increased by inflating the balloons once the needles are in position. By increasing the radius of curvature sufficiently relative to the separation between electrodes, the spatial uniformity of the heating can be enhanced. Chilled balloon inflation fluid can limit heating of the tissue adjacent the balloon.

The present invention further encompasses methods for teaching the above-described methods by demonstrating the methods of the present invention on patients, animals, physical or computer models, and the like.

While the exemplary embodiments have been described in some detail, by way of example and for clarity of understanding, a variety of modifications, adaptations, and changes will be obvious to those who skill in the art. For example, substantially coaxial cylindrical electrode surfaces may clamp tubular tissues (such as the cervix) between cooled parallel surfaces for treatment and/or shrinkage. Alternatively, a conductive liquid and an insulating liquid having differing densities may be used to selectively couple an electrode to a portion of a tissue surface within a body cavity, or substantially coaxial cylindrical electrode surfaces might clamp tubular tissues (such as the cervix) between cooled parallel surfaces for treatment and/or shrinkage. Therefore, the scope of the present invention is limited solely by the appended claims.

What is claimed is:

1. A method for therapeutically heating a target urinary continence support tissue within a patient body, the method comprising:

engaging a probe with a tissue adjacent to the target urinary continence support tissue;

pre-cooling the adjacent tissue with the probe according to a predetermined pre-cooling regimen comprising at least one of a predetermined pre-cooling time and a predetermined pre-cooling temperature; and heating the target urinary continence support tissue after pre-cooling the adjacent tissue by directing electrical current flux from the probe, through the pre-cooled adjacent tissue, and into the target urinary continence support tissue.

2. A method for heating a target continence support tissue within a patient body, the target continence support tissue separated from a tissue surface by an intermediate tissue, the method comprising:

coupling an electrode of a probe to the tissue surface;

pre-cooling the intermediate tissue with the probe according to a predetermined pre-cooling regimen comprising at least one of a predetermined pre-cooling time and a predetermined pre-cooling temperature; and intermittently energizing the electrode to heat the target continence support tissue through the pre-cooled intermediate tissue.

3. A method for selectively heating a predetermined target continence support tissue, the target continence support tissue adjacent another tissue, the method comprising:

generating a predetermined temperature differential between the adjacent tissue and the target continence support tissue by pre-cooling the adjacent tissue; and heating the target continence support tissue by conducting a heating electrical current into the target continence support tissue after generating the predetermined temperature differential so that the predetermined temperature differential urges the heating current from the adjacent tissue into the target continence support tissue.

4. The method of claim 3, wherein the pre-cooling of the adjacent tissue is performed so as to enhance an impedance of the adjacent tissue sufficiently to locally reduce current density within the adjacent tissue so that heating of the adjacent tissue by the heating current is significantly diminished.

5. The method of claim 3, further comprising controlling the pre-cooling step so as to align the temperature differential between the target continence support tissue and the adjacent tissue.

6. The method of claim 3, wherein the target continence support tissue and the adjacent tissue define a boundary region therebetween, and wherein at least a portion of the heating electrical current is sufficiently parallel to the boundary region that the temperature differential tailors heating by urging the current from the adjacent tissue to the target continence support tissue.

7. The method of claim 3, wherein the heating step effects shrinkage of the target continence support tissue, the target tissue comprising collagen.

8. The method of claim 7, wherein the target continence support tissue comprises an endopelvic support tissue, and wherein the shrinkage of the target support tissue inhibits incontinence.

9. A method for therapeutically heating a target zone of a urinary continence support tissue within a patient body, the method comprising:

engaging a tissue adjacent to the target zone of the urinary continence support tissue with a probe;

pre-cooling the adjacent tissue with the probe according to a predetermined pre-cooling regimen comprising selecting a desired tissue treatment depth based on at least one of a predetermined pre-cooling time and a predetermined pre-cooling temperature; and heating the target zone of the urinary continence support tissue after pre-cooling the adjacent tissue by directing electrical current flux from the probe, through the pre-cooled adjacent tissue, and into the target zone of the urinary continence support tissue.

10. A method for heating a target tissue within a patient body, the target continence support tissue separated from a tissue surface by an intermediate tissue, the method comprising:

coupling an electrode of a probe to the tissue surface;

pre-cooling the intermediate tissue with the probe according to a predetermined pre-cooling regimen comprising selecting a desired tissue treatment depth based on at least one of a predetermined pre-cooling time and a predetermined pre-cooling temperature; and intermittently energizing the electrode to heat the target continence support tissue through the pre-cooled intermediate tissue.

11. A method for selectively heating a predetermined target continence support tissue, the target continence support tissue adjacent another tissue, the method comprising:

generating a predetermined temperature differential between the adjacent tissue and the target continence support tissue by pre-cooling the adjacent tissue with the probe according to a predetermined pre-cooling regimen comprising selecting a desired tissue treatment depth based on at least one of a predetermined pre-cooling time and a predetermined pre-cooling temperature; and heating the target continence support tissue by conducting a heating electrical current into the target continence support tissue after generating the predetermined temperature differential so that the predetermined temperature differential urges the heating current from the adjacent tissue into the target continence support tissue.

12. The method of claim 11, wherein the pre-cooling of the adjacent tissue is performed so as to enhance an impedance of the adjacent tissue sufficiently to locally reduce current density within the adjacent tissue so that heating of the adjacent tissue by the heating current is significantly diminished.

13. The method of claim 11, further comprising controlling the pre-cooling step so as to align the temperature differential between the target continence support tissue and the adjacent tissue.

14. The method of claim 11, the target continence support tissue and the adjacent tissue define a boundary region therebetween, and wherein at least a portion of the heating electrical current is sufficiently parallel to the boundary region that the temperature differential tailors heating by urging the current from the adjacent tissue to the target continence support tissue.

15. The method of claim 11, wherein the heating step effects shrinkage of the target continence support tissue, the target continence support tissue comprising collagen.

16. The method of claim 15, wherein the target continence support tissue comprises an endopelvic support tissue, and wherein the shrinkage of the target tissue inhibits incontinence.

17. A method for therapeutically heating a target zone of a continence support tissue within a patient body that is accessible through one of a vagina, urethra, and sphincter, wherein the target zone is at a desired treatment depth relative to a surface of the tissue, the method comprising:

contacting the surface of the tissue with a probe;

selecting a predetermined pre-cooling regimen to allow for treatment to the desired treatment depth while reducing damage to the tissue adjacent to the target zone of the continence support tissue;

pre-cooling the tissue adjacent the target zone of the continence support tissue with the predetermined pre-cooling regimen; and directing an electrical current flux from the probe, through the pre-cooled tissue adjacent the target zone of the continence support tissue, and into the target zone of the continence support tissue.

18. The method of claim 17 wherein pre-cooling comprises reducing a temperature of tissue adjacent the target zone for a predetermined time period.

19. The method of claim 17 wherein pre-cooling comprises reducing a temperature of the tissue adjacent the target zone to a predetermined temperature level.

* * * * *